US008212078B2

(12) United States Patent
Lee et al.

(10) Patent No.: US 8,212,078 B2
(45) Date of Patent: Jul. 3, 2012

(54) DIIMINES AND SECONDARY DIAMINES

(75) Inventors: John Y. Lee, Baton Rouge, LA (US);
Paul L. Wiggins, Baton Rouge, LA (US); Judit Orgad, Baton Rouge, LA (US); Mahmood Sabahi, Baton Rouge, LA (US); Vernon O. Brandt, Baton Rouge, LA (US); David W. Owens, Baton Rouge, LA (US)

(73) Assignee: Albemarle Corporation, Richmond, VA (US)

( * ) Notice: Subject to any disclaimer, the term of this patent is extended or adjusted under 35 U.S.C. 154(b) by 1029 days.

(21) Appl. No.: 11/909,824

(22) PCT Filed: Dec. 30, 2005

(86) PCT No.: PCT/US2005/047696
§ 371 (c)(1),
(2), (4) Date: Sep. 27, 2007

(87) PCT Pub. No.: WO2006/104528
PCT Pub. Date: Oct. 5, 2006

(65) Prior Publication Data
US 2008/0194788 A1    Aug. 14, 2008

Related U.S. Application Data

(60) Provisional application No. 60/665,915, filed on Mar. 28, 2005.

(51) Int. Cl.
C07C 211/00 (2006.01)
(52) U.S. Cl. ........ 564/306; 564/248; 564/448; 564/461; 564/462; 528/68
(58) Field of Classification Search .......................... None
See application file for complete search history.

(56) References Cited

U.S. PATENT DOCUMENTS

| | | |
|---|---|---|
| 2,380,420 A | 7/1945 | Emerson |
| 2,497,292 A | 2/1950 | Bruner |
| 2,582,128 A | 1/1952 | Hurwitz et al. |
| 2,953,579 A | 9/1960 | Williams et al. |
| 2,965,605 A | 12/1960 | Reynolds et al. |
| 3,209,030 A | 9/1965 | Bicek |
| 3,275,567 A | 9/1966 | Keith et al. |
| 3,336,386 A | 8/1967 | Dovell et al. |
| 3,350,450 A | 10/1967 | Dovell et al. |
| 3,414,616 A | 12/1968 | Summers |
| 3,519,603 A | 7/1970 | Lohse et al. |
| 3,538,161 A | 11/1970 | Dovell |
| 3,609,121 A | 9/1971 | Lohse et al. |
| 3,625,710 A | 12/1971 | Rizzi |
| 3,658,937 A | 4/1972 | Terni et al. |
| 3,761,425 A | 9/1973 | Baessler et al. |
| 3,937,730 A | 2/1976 | Vogel et al. |
| 3,943,158 A | 3/1976 | Dietrich et al. |
| 3,952,056 A | 4/1976 | Vogel et al. |
| 3,994,975 A | 11/1976 | Oude Alink et al. |
| 4,045,486 A | 8/1977 | Krall et al. |
| 4,140,718 A | 2/1979 | Symon |
| 4,161,492 A | 7/1979 | Weissel |
| 4,317,916 A | 3/1982 | Degischer et al. |
| 4,373,107 A | 2/1983 | Tahara et al. |
| 4,521,624 A | 6/1985 | Jackisch |
| 4,528,363 A | 7/1985 | Tominaga |
| 4,631,298 A | 12/1986 | Presswood |
| 4,663,201 A | 5/1987 | House et al. |
| 4,714,512 A | 12/1987 | House et al. |
| 4,760,183 A | 7/1988 | Papenfuhs et al. |
| 4,789,691 A | 12/1988 | Matzke et al. |
| 4,806,616 A | 2/1989 | Baumann et al. |
| 4,900,868 A | 2/1990 | Merten et al. |
| 4,925,974 A | 5/1990 | Gras |

(Continued)

FOREIGN PATENT DOCUMENTS

CA    1218190 A    2/1987

(Continued)

OTHER PUBLICATIONS

Wang et al., "Bolaamphiphilic Single-Chain Bis-Schiff Base Derivatives: Aggregation and Thermal Behavior in Aqueous Solution." Langmuir, 2001, vol. 17, p. 3162-3167.
Adams et al., "Restricted Rotation in Aryl Amines. XIV. Isopropyl Derivatives of Dibenzenesulfonamidomesitylene", J. Am. Chem. Soc., 1950, pp. 5077-5079, vol. 72.
Arunajatesan, V., et al., "Optimization of Reductive Alkylation Catalysts by Experimental Design", Organic Reactions Catalysis Society, 2007, pp. 481-485.

(Continued)

Primary Examiner — Sudhakar Katakam
(74) Attorney, Agent, or Firm — James A. Jubinsky

(57) ABSTRACT

This invention provides aromatic diimines where the diimines have imino groups with at least two carbon atoms, and either are in the form of one benzene ring having two imino groups on the ring, which imino groups are meta or para relative to each other, and in which each position ortho to an imino group bears a hydrocarbyl group, or are in the form of two benzene rings connected by an alkylene bridge and having one imino group on each ring, and in which each position ortho to an imino group bears a hydrocarbyl group. This invention also provides aromatic secondary diamines where the diamines have amino hydrocarbyl groups with at least two carbon atoms, and either are in the form of one benzene ring having two amino groups on the ring, which amino groups are meta or para relative to each other, and in which each position ortho to an amino group bears a hydrocarbyl group, or are in the form of two benzene rings connected by an alkylene bridge and having one amino group on each ring, and in which each position ortho to an amino group bears a hydrocarbyl group. Also provided are processes for forming diimines and secondary diamines from primary diamines, including the aromatic diimines and aromatic secondary diamines of the invention.

1 Claim, No Drawings

U.S. PATENT DOCUMENTS

| | | | |
|---|---|---|---|
| 5,001,267 | A | 3/1991 | Speranza et al. |
| 5,002,806 | A | 3/1991 | Chung |
| 5,008,453 | A | 4/1991 | Nalepa et al. |
| 5,041,668 | A | 8/1991 | Nalepa et al. |
| 5,145,825 | A | 9/1992 | Deeba et al. |
| 5,312,886 | A | 5/1994 | House et al. |
| 5,430,188 | A | 7/1995 | Bader et al. |
| 5,470,890 | A | 11/1995 | House et al. |
| 5,498,585 | A | 3/1996 | Bartels et al. |
| 5,616,799 | A | 4/1997 | Planker et al. |
| 5,646,235 | A | 7/1997 | Zimmerman et al. |
| 5,744,642 | A | 4/1998 | Lantzsch et al. |
| 5,847,067 | A | 12/1998 | Gras |
| 5,859,164 | A | 1/1999 | Gras et al. |
| 6,013,755 | A | 1/2000 | Primeaux, II et al. |
| 6,103,799 | A * | 8/2000 | Lassila et al. ............... 524/251 |
| 6,156,863 | A | 12/2000 | Wenning |
| 6,218,480 | B1 | 4/2001 | Rappoport |
| 6,399,736 | B1 | 6/2002 | Primeaux, II et al. |
| 6,403,752 | B1 | 6/2002 | House et al. |
| 6,429,338 | B1 | 8/2002 | Burdeniuc et al. |
| 6,444,721 | B2 | 9/2002 | Schwalm et al. |
| 6,803,445 | B2 | 10/2004 | Ishikawa et al. |
| 7,288,677 | B2 | 10/2007 | Lee et al. |
| 7,767,858 | B2 | 8/2010 | Wiggins et al. |
| 2002/0028901 | A1 | 3/2002 | Gunatillake et al. |
| 2004/0015016 | A1 | 1/2004 | Su et al. |
| 2004/0019238 | A1 | 1/2004 | Su et al. |
| 2004/0054150 | A1 | 3/2004 | Murray |
| 2004/0180778 | A1 | 9/2004 | Small |
| 2007/0066786 | A1 | 3/2007 | Hanson, Jr. et al. |
| 2007/0073030 | A1 | 3/2007 | Wiggins et al. |
| 2007/0270566 | A1 | 11/2007 | Lee et al. |
| 2008/0004406 | A1 | 1/2008 | Lee et al. |

FOREIGN PATENT DOCUMENTS

| | | |
|---|---|---|
| CN | 1352202 | 6/2002 |
| DE | 1163315 | 2/1964 |
| DE | 2940738 A1 | 4/1981 |
| DE | 264014 A1 | 1/1989 |
| DE | 3728141 | 3/1989 |
| DE | 19701835 A1 | 7/1998 |
| DE | 102005046641 A1 | 4/2007 |
| EP | 0014985 A1 | 9/1980 |
| EP | 0288067 A1 | 10/1988 |
| EP | 0309980 A1 | 4/1989 |
| EP | 0420426 A2 | 4/1991 |
| EP | 0469751 A1 | 2/1992 |
| EP | 0688802 A1 | 12/1995 |
| EP | 0779278 A3 | 6/1997 |
| EP | 0802209 B1 | 10/1997 |
| EP | 1067116 A1 | 1/2001 |
| EP | 1229020 A1 | 8/2002 |
| GB | 1070759 | 6/1967 |
| GB | 1320863 | 6/1973 |
| GB | 1478446 | 6/1977 |
| JP | 63052146 A2 | 3/1988 |
| JP | 5274914 A2 | 10/1993 |
| JP | 09100260 A | 4/1997 |
| RU | 387551 | 3/1973 |
| WO | WO-92/18575 A1 | 10/1992 |
| WO | WO-97/01529 | 1/1997 |
| WO | WO-00/26181 A1 | 5/2000 |
| WO | WO-02/102869 A1 | 12/2002 |
| WO | WO-03/018531 A1 | 3/2003 |
| WO | WO-2004/073634 A2 | 9/2004 |
| WO | WO-2005/033119 A1 | 4/2005 |
| WO | WO-2006/028728 A1 | 3/2006 |

OTHER PUBLICATIONS

Barmetter, "Acid-Catalyzed [3.3]-Sigmatropic Rearrangements of N-Propargylanilines", Helvetica Chimica Acta, 1990, pp. 1515-1573, vol. 73, Verlag Helvetica Chimica Acta, Basel, CH.

Billaud et al., "Quantitative Analysis of Epoxy Resin Cure Reaction: A Study by Near-Infrared Spectroscopy", Applied Spectroscopy, 2002, pp. 1413-1421, vol. 56(11).

Borges-Lopes et al., "Synthesis and Characterization of New Methyl-Substituted Azomethine-Siloxane Liquid Crystal Macrocycles Influence of the Methyl-Substitution on the Cycle Formation", Polymer Bulletin, 1995, pp. 523-530, vol. 34, Springer, Heidelberg, Berlin, DE.

Campbell et al., "The Preparation of Unsymmetrical Secondary Aliphatic Amines", J. Am. Chem. Soc., 1944, pp. 82-84, vol. 66.

Childs et al., "Assembly of a Nanoscale Chiral Ball Through Supramolecular Aggregation of Bowl-Shaped Triangular Helicates", Angewandte Chemie, 2002, pp. 4244-4247, vol. 41, VCH Verlagsgesellschaft, Weinheim, DE.

Childs et al., "Using Noncovalent Intra-strand and Inter-strand Interactions to Prescribe Helix Formation within a Metallo-supramolecular System", Chem. Eur. J., 2004, pp. 4291-4300, vol. 10(17).

Deschenaux et al., "Structural Isomerism in Polycondensates. IV. Synthesis and Characterization of Liquid Crystalline Poly(azomethines) and Low Molecular Weight Model Compounds", Helvetica Chimica Acta, 1986, pp. 1349-1355, vol. 69(6).

Distefano, "Reinvestigation of the Formaldehyde-Aniline Condensation. Part 4. Ultraviolet Photoelectron and Electron Transmission Spectra of N-Methyleneaniline and its Symmetric Dimethyl Ring-substituted Homologues and Semiempirical Theoretical Evaluations", J. Chem. Soc. Perkin Trans II, 1985, pp. 1623-1627.

Dovell & Greenfield, "Platinum Metal Sulfides as Heterogeneous Hydrogenation Catalysts", J. Am. Chem. Soc., 1965, pp. 2767-2768, vol. 87.

Dvolaitzky et al., "Stable N,N'-di-tert-butyl-meta-phenylenebisnitroxides-Unexpected Ground-State Singlets", Angewandte Chemie Int. Ed. Engl., 1992, pp. 180-181, vol. 31(2).

Emerson et al., "The Reductive Alkylation of Hindred Aromatic Primary Amines", J. Am. Chem. Soc., 1941, pp. 972-974, vol. 63.

Hine, et al., "Polar Effects on the Formation of Imines from Isobutyraldehyde and Primary Aliphatic Amines", The Journal of Organic Chemistry, 1970, pp. 340-344, vol. 85.

Jie et al., "Bridged Bis-Pyridinylimino Dinickel (II) Complexes: Syntheses, Characterization, Ethylene Oligomerization and Polymerization", Journal of Organometallic Chemistry, 2005, pp. 1739-1749, vol. 690, Elsevier-Sequoia S.A. Lausanne, CH.

Klebanskii, A. L., et al., "Synthesis and Polycondensation of N-alkyl Derivatives of Hexamethylenediamine. I. Synthesis of N,N'-dialkyl Derivatives of Hexamethylenediamine", Zhurnal Obshchei Khimii, 1958, 28, 1066-72. CAPLUS abstract 1958:103796, 1 page.

Lai, J.T., "Ketoform Reaction. Synthesis of Hindered Imines from 2,6-dialkylanilines and Ketones", Tetrahedron Letters, 2002, p. 1965-1967; 1996, vol. 43, Elsevier Science Publishers, Amsterdam, NL.

Layer, Robert W.; "The Chemistry of Imines", Chemical Reviews; 1963; vol. 63; pp. 489-510.

Luo et al., "New Bi-nuclear and Multi-nuclear α-diimine/nickel Catalysts for Ethylene Polymerization", Journal of Molecular Catalysts, 2005, pp. 153-161, vol. 227.

March, "Reactions, Mechanisms, and Structure", Advanced Organic Chemistry, 1992, pp. 896-900, 4$^{th}$ Ed., John Wiley & Sons, US.

Mi et al., "Homo- and Copolymerization of Norbornene and Styrene with Pd- and Ni-Based Novel Bridged Dinuclear Diimine Complexes and MAO",Macromol. Chem. Phys., 2003, pp. 868-876, vol. 204(5/6).

Mylroie, Victor L., et al., "Reductive Alkylation Optimized by Techniques of Experimental Design", Catalysis of Organic Reactions, Chem. Ind. Series, vol. 68, Marcel Dekker, New York, 1996, pp. 301-312.

Pal et al., "Schiff Base Linked Ferrocenyl Complexes for Second-Order Nonlinear Optics", Journal of Organometallic Chemistry, 2000, pp. 248-259, vol. 604, Elsevier-Sequoia S.A., Lausanne, CH.

Parker, et al., "Reaction Chemistry of Tri-Substituted Mesitylene derivatives and the Synthesis of Sterically Buttressed 1,3,5-triaminocyclohexyl Ligands", J. Chem. Soc., Perkin Transactions 2, Chemical Society, 1997, pp. 1445-1452.

Patai, The Chemistry of the Carbon-Nitrogen Double Bond, 1970, pp. 61-67, 130, 255-256, 276-293, 296-298, Interscience Publishers, Great Britain.

Perez, Jr. et al., "Performance and Processing Enhancements of Aromatic Polyurea Elastomer Systems Prepared from High 2,4'-MDI Isocyanates", Huntsman Corporation; 3 pages.

Posey et al., "New Secondary Amine Chain Extenders for Aliphatic Polyurea Materials", Polyurea Development Association 2003 Annual Conference, Aug. 19-21, 2003, John Ascuaga's Nugget Casino Resort, Reno, NV; 11 pages.

Rylander, "Reduction Alkylation", Catalytic Hydrogenation in Organic Syntheses, 1979, pp. 165-174, Academic Press, New York, NY, USA.

Smith et al., "Preparation of Polyimides Utilizing the Diels-Alder Reaction. 1,4-N,N'-Bis(Butadienyl-2-Methyl) Diamido)-2,3,5,6-tetramethylbenzenes with Bismaleimides", Macromolecules, American Chemical Society, 1996, pp. 1123-1130, vol. 29, Easton, US.

Sun et al., "Supramolecular Helical Architecture Assembled by Double-Helical [$Ag_2L_2$] Units", Journal of Organometallic Chemistry, 2004, pp. 43-49, vol. 689.

Taneda et al., "Photochromism of Polymorphic 4, 4'-methylenebis-(N-salicylidene-2, 6-diisopropylaniline) Crystals", Org. Biomol. Chem., 2004, pp. 499-504, vol. 2(4).

Trost et al., "Dehydrogenation of Amines. An approach to Imines and Aldehydes", The Journal of Organic Chemistry, 1981, pp. 4617-4620, vol. 46.

Voigt-Martin et al., "Structure and Defects in Sanidic Liquid Crystalline Polymers. 2. Structure Analysis of Sanidic Polymers by Simulation of Diffraction Patterns From Monomeric Analogs", Macromolecules, 1995, pp. 243-254, vol. 28(1).

CAPLUS Abstract of Vasilenko et al., "Electron Spectra and Structure of Molecules Containing a Carbon:Nitrogen Group. II. Absorption Spectra of Benzyideneaniline Derivatives and Bis(azomethines)", Zhurnal Fizicheskoi Khimii; 1976; 50(3); pp. 597-601; Accession No. 1976:405028.

CAPLUS Abstract of Zhang et al., "Synthesis of Bis-(salicylaldininato) Nickel Complexes and Their Catalytic Behavior for Vinyl Polymerization of Norbornene"; Gaofenzi Xuebao; 2004; (5); pp. 758-762; Accession No. 2004:985377.

Johnson Matthey Catalysts & Chemicals Division, Heterogeneous Catalyst Application Table, date uncertain, Nov. 18, 2005, or earlier.

Shepherd, R. G., et al., "Antituberculous Agents. II. N,N'-Diisopropylethylenediamine and Analogs", Journal of Medicinal & Pharmaceutical Chemistry, 1962, vol. 5, pp. 823-835.

* cited by examiner

DIIMINES AND SECONDARY DIAMINES

REFERENCE TO RELATED APPLICATIONS

This application is the National Stage of International Patent Application PCT/US2005/47696, filed on Dec. 30, 2005, which application claims priority from U.S. Application No. 60/665,915, filed Mar. 28, 2005, the disclosures of which are incorporated herein by reference.

Reference is hereby made to U.S. application Ser. No. 11/390,777, filed Mar. 27, 2006, now U.S. Pat. No. 7,288,677, issued on Oct. 30, 2007, which Application claims priority from Application No. 60/665,915, filed Mar. 28, 2005.

TECHNICAL FIELD

This invention relates to the preparation of diimines and secondary diamines from primary diamines, and to new aromatic diimines and new aromatic secondary diamines.

BACKGROUND

There are many polyfunctional compounds, including diols and aromatic diamines, which are indicated to be useful as chain extenders in the preparation of polyurethane, polyurea, and polyurethane-urea polymers and/or as curing agents for epoxy resins. None of these compounds has a reactivity such as to make it universally ideal, and many fail to provide satisfactory properties in the products made by their use. Thus, there is still a need to find new compounds capable of serving as chain extenders or curing agents. U.S. Pat. No. 4,806,616 teaches the use of certain N,N'-dialkylphenylenediamines as chain extenders in preparing polyurethanes and polyureas. In this connection, also see for example U.S. Pat. No. 4,528,363, which teaches the use of secondary aliphatic diamines as part of a resin binder, and U.S. Pat. No. 6,218,480 B1, which discloses use of aromatic diamines as hardeners for polyurethanes. Secondary aromatic diamines have also been used as anti-degradants for rubber; see U.S. Pat. No. 4,900,868.

Imines are often formed from combination of a primary amine and an aldehyde or ketone. Such imines can be used as flavors (see U.S. Pat. No. 3,625,710) or fragrances (see EP 1067116).

To date, it has not been found possible to obtain aromatic diimines having groups with two or more carbon atoms from aromatic primary diamines where the two amino groups are either on one phenyl ring, or one amino group is on each of two phenyl rings, where the two phenyl rings are connected via an alkylene bridge, and in which each position ortho (immediately adjacent) to each amino group bears a hydrocarbyl substituent. Attempts to prepare diimines via reaction of such primary diamines with acetaldehyde or acetone in the presence or absence of catalysts have not worked; see U.S. Pat. Nos. 5,041,668 and 5,008,453. It had been indicated that the presence of an aryl group on the nitrogen or carbon of an imine group stabilized the imine; however, it has been reported that at least some of the compounds previously believed to be stable aromatic imines had been misidentified and were really polymers formed from unstable imines. In this connection, see Distefano et al., *J. Chem. Soc. Perkin Trans. II*, 1985, pp. 1623-1627.

It would be desirable to have routes to such diimines, and to have routes to aromatic secondary diamines that can be obtained from such diimines. There is a growing need for chain extenders with slower cure rates, so it would be a further advantage if these aromatic secondary diamines exhibited slower curing rates than those of presently available chain extenders.

SUMMARY OF INVENTION

This invention in part provides processes for preparing diimines in which the imino hydrocarbylidene groups have at least two carbon atoms, where the diimine is (a) an aromatic diimine which is either in the form of one benzene ring having two imino groups on the ring, in which each position ortho to an imino group (—N═R) bears a hydrocarbyl group, or in the form of two benzene rings connected by an alkylene bridge and having one imino group on each ring, in which each position ortho to an imino group bears a hydrocarbyl group, (b) an aromatic diimine which is either in the form of one benzene ring having two imino groups on the ring or in the form of two benzene rings connected by an alkylene bridge and having one imino group on each ring, in which at least one position ortho to each imino group has a hydrogen atom as a substituent, or (c) an aliphatic diimine, where the diimine is made by reacting a primary diamine with at least one ketone and/or aldehyde. The art teaches that diimines of type (a) could not be made. These aromatic diimines, which surprisingly can be made, are compositions of the invention. Aromatic secondary diamines made from aromatic diimines of type (a) are also compositions of the invention. Surprisingly, such aromatic secondary diamines exhibit slower curing rates than those of presently available chain extenders. Slower cure rates are desirable for certain proprietary commercial applications. By hydrogenating (reducing) aromatic diimines of type (a), the corresponding novel aromatic secondary diamines of the invention are formed. Processes for forming secondary diamines, including the aromatic secondary diamines that are compositions of the invention, from primary diamines in one step are also provided by this invention. In all of the processes of this invention, relatively mild pressure and temperature conditions are used; advantageously, ordinary process apparatus can be employed, so there is no need for specialized equipment, such as that required for high-pressure reactions. This is of particular significance in processes where hydrogen gas is employed in the formation of secondary diamines. The process technology of this invention can be used to prepare a wide variety of known diimines and secondary diamines via reaction of primary diamines with ketones or aldehydes.

One embodiment of this invention provides, as new compositions of matter, aromatic diimines wherein the diimine either is in the form of one benzene ring having two imino groups on the ring, which imino groups are meta or para relative to each other, and in which each position ortho to an imino group bears a hydrocarbyl group, or is in the form of two benzene rings connected by an alkylene bridge and having one imino group on each ring, wherein each position ortho to an imino group bears a hydrocarbyl group, and wherein each imino hydrocarbylidene group has at least two carbon atoms. The aromatic diimines of the invention can be represented by the structures:

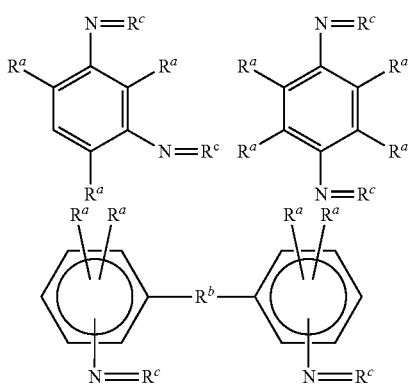

where each $R^a$ may be the same or different, and each $R^a$ is a hydrocarbyl group, $R^b$ is an alkylene bridge, and each $R^c$ is a hydrocarbylidene group having at least two carbon atoms.

Another embodiment of this invention provides, as new compositions of matter, aromatic secondary diamines where the secondary diamine either is in the form of one benzene ring having two secondary amino groups on the ring, which secondary amino groups are meta or para relative to each other, and in which each position ortho to a secondary amino group bears a hydrocarbyl group, or is in the form of two benzene rings connected by an alkylene bridge and having one secondary amino group on each ring, wherein each position ortho to a secondary amino group bears a hydrocarbyl group, and wherein each amino hydrocarbyl group has at least two carbon atoms. The aromatic secondary diamines of the invention can be represented by the structures:

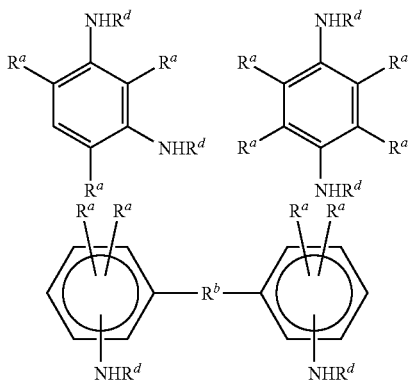

where each $R^a$ may be the same or different, and each $R^a$ is a hydrocarbyl group, $R^b$ is an alkylene bridge, and each $R^d$ is a hydrocarbyl group having at least two carbon atoms.

Another embodiment of this invention is a process for forming a secondary diamine. The process comprises mixing together at least one ketone or aldehyde, at least one acid ion exchange resin, at least one hydrogenation agent, and at least one primary diamine, such that a secondary diamine is formed. The primary diamine is I) an aromatic primary diamine which is either in the form of one benzene ring having two primary amino groups on the ring or in the form of two benzene rings connected by an alkylene bridge and having one primary amino group on each ring, wherein at least one position ortho to each primary amino group has a hydrogen atom as a substituent, or II) an aromatic primary diamine which is either in the form of one benzene ring having two primary amino groups on the ring, which primary amino groups are meta or para relative to each other or is in the form of two benzene rings connected by an alkylene bridge and having one primary amino group on each ring, wherein each position ortho to a primary amino group bears a hydrocarbyl group, or III) an aliphatic primary diamine. When the primary diamine is I), the hydrogenation agent is a hydride transfer agent, a dissolving metal reagent, a borane reductant, or hydrogen with a hydrogenation catalyst, where the hydrogenation catalyst is sulfided platinum on carbon, sulfided palladium on carbon, or a mixture thereof. When the primary diamine is II), the hydrogenation agent is a dissolving metal reagent or hydrogen with a hydrogenation catalyst, where the hydrogenation catalyst is sulfided platinum on carbon, sulfided palladium on carbon, or a mixture thereof, or is selected from the group consisting of palladium on carbon, platinum on carbon, and a mixture of both of these, when used with hydrogen sulfide or at least one strong acid. When the primary diamine is III), the hydrogenation agent is a hydride transfer agent, a dissolving metal reagent, a borane reductant, or hydrogen with a hydrogenation catalyst, where the hydrogenation catalyst is sulfided platinum on carbon, sulfided palladium on carbon, or a mixture thereof.

Still another embodiment of this invention is a process for forming a diimine. The process comprises mixing together at least one ketone or aldehyde, at least one acid ion exchange resin, and at least one primary diamine, such that a diimine is formed. The primary diamine is I) an aromatic primary diamine which is either in the form of one benzene ring having two primary amino groups on the ring or in the form of two benzene rings connected by an alkylene bridge and having one primary amino group on each ring, wherein at least one position ortho to each primary amino group has a hydrogen atom as a substituent, or II) an aromatic primary diamine which is either in the form of one benzene ring having two primary amino groups on the ring, which primary amino groups are meta or para relative to each other or is in the form of two benzene rings connected by an alkylene bridge and having one primary amino group on each ring, wherein each position ortho to a primary amino group bears a hydrocarbyl group, or III) an aliphatic primary diamine. Often this process further comprises mixing together at least a portion of the diimine and a hydrogenation agent. When the primary diamine used in forming the diimine is I) or III), the hydrogenation agent is a hydride transfer agent, a dissolving metal reagent, a borane reductant, or hydrogen with a hydrogenation catalyst, wherein the hydrogenation catalyst is sulfided platinum on carbon, sulfided palladium on carbon or a mixture thereof. When the primary diamine used in forming the diimine is II), the hydrogenation agent is a dissolving metal reagent or hydrogen with a hydrogenation catalyst, where the hydrogenation catalyst is sulfided platinum on carbon, sulfided palladium on carbon, or a mixture thereof, or is selected from the group consisting of palladium on carbon, platinum on carbon, and a mixture of both of these, when used with hydrogen sulfide or at least one strong acid, such that a secondary diamine is formed.

Another embodiment of this invention is a process for forming an aromatic secondary diamine. The process comprises mixing together at least one ketone or aldehyde, hydrogen, a hydrogenation catalyst selected from sulfided platinum on carbon, sulfided palladium on carbon, and a mixture thereof, and at least one primary diamine, such that a secondary diamine is formed. When the primary diamine is I) an aromatic primary diamine which is either in the form of one benzene ring having two primary amino groups on the ring or in the form of two benzene rings connected by an alkylene bridge and having one primary amino group on each ring, wherein at least one position ortho to each primary amino group has a hydrogen atom as a substituent, the process is conducted at a temperature in the range of about 20° C. to about 120° C. and at a hydrogen pressure in the range of about 14 to about 125 pounds per square inch. When the primary diamine is II) an aromatic primary diamine which is either in the form of one benzene ring having two primary amino groups on the ring, which primary amino groups are meta or para relative to each other or is in the form of two benzene rings connected by an alkylene bridge and having one primary amino group on each ring, wherein each position ortho to a primary amino group bears a hydrocarbyl group, the process is conducted at a temperature in the range of about 75° C. to about 140° C. and at a hydrogen pressure in the range of about 14 to about 150 pounds per square inch. When the primary diamine is III) an aliphatic primary diamine, the process is conducted at a temperature in the range of about 20° C. to about 140° C. and at a hydrogen pressure in the range of about 14 to about 150 pounds per square inch.

A further embodiment of the invention is a formulation which is formed from ingredients comprising at least one polyol and/or at least one polyetheramine, at least one isocyanate, and at least one aromatic secondary diamine. The aromatic secondary diamine is at least one of the aromatic secondary diamines described above as new compositions of matter.

A still further embodiment of the invention is a method for producing a polyurethane, polyurea, or polyurea-urethane. The method comprises blending at least one polyol and/or at least one polyetheramine, at least one isocyanate, and at least one aromatic secondary diamine. The aromatic secondary diamine is at least one of the aromatic secondary diamines described above as new compositions of matter.

These and other embodiments and features of this invention will be still further apparent from the ensuing description and appended claims.

FURTHER DETAILED DESCRIPTION OF THE INVENTION

Certain terms that are commonly used in the art can be used to refer to various aspects of the present invention. Imines that are products of a reaction of a primary amine and a carbonyl compound are sometimes called Schiff bases, and such imines are formed by at least some of the processes of the invention. When the carbonyl compound used to form the imine is a ketone, such an imine is occasionally referred to as a ketimine; similarly, when the carbonyl compound used to form the imine is an aldehyde, such an imine is occasionally referred to as an aldimine. The formation of a secondary amine from a primary amine and an aldehyde or ketone is often referred to as reductive alkylation or reductive amination, and the terms "reductive alkylation" and "reductive amination" can be used to describe some of the processes of the invention.

Those of skill in the art will recognize that there are several ways to name the aromatic primary diamines used in the processes of the invention, as well as the aromatic diimines and the aromatic secondary diamines that are compositions of the invention. For example, the structure

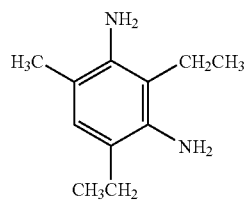

which represents a particularly preferred aromatic primary diamine in the processes of the invention, can be called 2,4-diethyl-6-methyl-1,3-benzenediamine, 2,4-diethyl-6-methyl-1,3-phenylenediamine, 3,5-diethyl-2,4-diaminotoluene, or 3,5-diethyl-toluene-2,4-diamine. Similarly, the structure

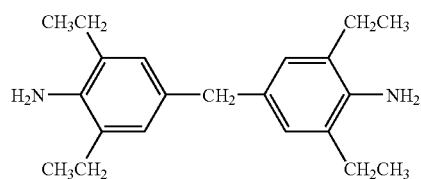

which represents another particularly preferred aromatic primary diamine in the processes of the invention, can be called 4,4'-methylenebis(2,6-diethylbenzeneamine), 4,4'-methylenebis(2,6-diethylaniline), or 3,3',5,5'-tetraethyl-4,4'-diaminodiphenylmethane.

While the term "secondary diamine" is used throughout this document to refer to diamines produced by the processes of this invention in which both amino groups are secondary, it is to be understood that the processes of this invention produce diamines in which only one of the amino groups is secondary (and the other amino group is primary), albeit usually in small amounts, because the processes of the invention do not necessarily produce diamine(s) where both amino groups are secondary in 100% yield. When the term "aromatic secondary diamine" is used to refer to compositions of the invention, it does not generally include aromatic diamines in which one amino group is secondary and the other amino group is primary, except as impurities present (usually in small amounts) in the aromatic secondary diamines.

Compositions of the Invention

A. Aromatic Diimines

An aromatic diimine which is a composition of this invention has at least two carbon atoms in each imino hydrocarbylidene group, and the diimine either is in the form of one benzene ring having two imino groups on the ring, which imino groups are meta or para relative to each other, and in which each position ortho (immediately adjacent) to an imino group (—N═R) bears a hydrocarbyl group, or is in the form of two benzene rings connected by an alkylene bridge and having one imino group on each ring, and in which each position ortho (immediately adjacent) to an imino group bears a hydrocarbyl group. The hydrocarbyl groups on the benzene rings may be the same or different. Examples of suitable hydrocarbyl groups on the aromatic ring include methyl, ethyl, propyl, isopropyl, n-butyl, sec-butyl, t-butyl, pentyl, cyclopentyl, hexyl, methylcyclohexyl, heptyl, octyl, cyclooctyl, nonyl, decyl, dodecyl, phenyl, benzyl, and the like. When the aromatic diimine is in the form of two benzene rings connected by an alkylene bridge and having one imino group on each ring and the imino group is adjacent (ortho) to the alkylene bridge, the alkylene bridge is considered as a hydrocarbyl group ortho to the imino group. Preferred hydrocarbyl groups on the benzene ring(s) (ortho to an imino group) of the aromatic diimines are straight-chain or branched-chain alkyl groups having from one to about six carbon atoms; particularly preferred hydrocarbyl groups are methyl, ethyl, isopropyl, butyl, and mixtures of two or more of these groups. Here, the preference for butyl groups includes n-butyl, sec-butyl, and t-butyl groups. The alkylene bridge of the two-ringed diimine has from one to about six carbon atoms; preferably, the bridge has from one to about three carbon atoms. More preferably, the alkylene bridge has one or two carbon atoms; highly preferred is an alkylene bridge having one carbon atom, i.e., a methylene group.

The hydrocarbylidene groups of the imino groups of the aromatic diimine generally have from two to about twenty carbon atoms; the hydrocarbylidene groups may be aliphatic (straight chain, branched, or cyclic) or aromatic. Preferably, the imino hydrocarbylidene groups are straight chain or branched chain alkylidene groups having from three to about six carbon atoms. Examples of suitable imino hydrocarbylidene groups include ethylidene, propylidene, isopropylidene, 1-cyclopropylethylidene, n-butylidene, sec-butylidene, cyclobutylidene, 2-ethylbutylidene, 3,3-dimethyl-2-butylidene, 3-pentylidene, 3-penten-2-ylidene, cyclopentylidene, 2,5-dimethylcyclopentylidene, 2-cyclopentenylidene, hexylidene, methylcyclohexylidene, menthylidene, ionylidene, phorylidene, isophorylidene, heptylidene, 2,6,-dimethyl-3-heptylidene, cyclooctylidene, 5-nonylidene, decylidene, 10-undecenylidene, benzylidene, 2,4-dimethylbenzylidene, 2-phenylethylidene, 1-phenylpentylidene, 1-naphthylidene, 2-naphthylidene, 1-naphthylethylidene, and the like. Particularly preferred imino hydrocarbylidene groups are isopropylidene and sec-butylidene.

Aromatic diimines having two imino groups on one benzene ring preferably have the imino groups meta relative to each other. In these preferred diimines, the imino hydrocarbylidene group preferably is a straight chain or branched chain alkylidene group having from three to about six carbon atoms. Particularly preferred are aromatic diimines in which the hydrocarbyl group between the two meta imino groups is a methyl group, while the two remaining hydrocarbyl groups are ethyl groups, and those in which the hydrocarbyl group between the two meta imino groups is an ethyl group, while one of the two remaining hydrocarbyl groups is a methyl group and the other is an ethyl group, and mixtures thereof, especially when the imino hydrocarbylidene groups are isopropylidene or sec-butylidene.

Preferred aromatic diimines in which one imino group is on each of two benzene rings, where the two benzene rings are connected via an alkylene bridge, have both imino groups para relative to the alkylene bridge. A particularly preferred aromatic diimine of this type is a compound where each hydrocarbyl group ortho to an imino group is an ethyl group and the alkylene bridge is a methylene group; this is especially preferred when the imino hydrocarbylidene groups are isopropylidene or sec-butylidene.

Diimines of the invention having both imino groups on one benzene ring include, but are not limited to, N,N'-diisopropylidene-2,4,6-triethyl-1,3-benzenediamine, N,N'-di-sec-butylidene-2,4,6-triethyl-1,3-benzenediamine, N,N'-di(2-pentylidene)-(2,4,6-triethyl-1,3-benzenediamine), N,N'-diisopropylidene-(2,4-diethyl-6-methyl-1,3-benzenediamine), N,N'-di-sec-butylidene-(2,4-diethyl-6-methyl-1,3-benzenediamine), N,N'-diisopropylidene-(4,6-diethyl-2-methyl-1,3-benzenediamine), N,N'-di-sec-butylidene-(4,6-diethyl-2-methyl-1,3-benzenediamine), N,N'-dicyclobutylidene-(4,6-diethyl-2-methyl-1,3-benzenediamine), N,N'-dicyclopentylidene-(2,4-diisopropyl-6-methyl-1,3-benzenediamine), N,N'-diisopropylidene-(2-methyl-4,6-di-sec-butyl-1,3-benzenediamine), N,N'-di(1-cyclopropylethylidene)-(2-methyl-4,6-di-sec-butyl-1,3-benzenediamine), N,N'-di(3,3-dimethyl-2-butylidene)-(2-ethyl-4-isopropyl-6-methyl-1,3-benzenediamine), N,N'-di(2-butenylidene)-2,4,5,6-tetra-n-propyl-1,3-benzenediamine, N,N'-di-sec-butylidene-2,3,5,6-tetraethyl-1,4-benzenediamine, and N,N'-di(2-phenylethylidene)-2,3,5,6-tetraethyl-1,4-benzenediamine. Particularly preferred aromatic diimines having both imino groups on one benzene ring are N,N'-diisopropylidene-(2,4-diethyl-6-methyl-1,3-benzenediamine), N,N'-diisopropylidene-(4,6-diethyl-2-methyl-1,3-benzenediamine), and mixtures thereof; N,N'-di-sec-butylidene-(2,4-diethyl-6-methyl-1,3-benzenediamine), N,N'-di-sec-butylidene-(4,6-diethyl-2-methyl-1,3-benzenediamine), and mixtures thereof.

Examples of aromatic diimines of the invention in which one imino group is on each of two benzene rings include N,N'-diisopropylidene-2,2'-methylenebis(6-n-propylbenzeneamine), N,N'-di-sec-butylidene-2,2'-methylenebis(6-n-propylbenzeneamine), N,N'-di-sec-butylidene-2,2'-methylenebis(3,6-di-n-propylbenzeneamine), N,N'-di(1-cyclobutylethylidene)-2,2'-methylenebis(5,6-dihexylbenzeneamine), N,N'-diisopropylidene-3,3'-methylenebis(2,6-di-n-butylbenzeneamine), N,N'-di(2,4-dimethyl-3-pentylidene)-3,3'-methylenebis(2,6-di-n-butylbenzeneamine), N,N'-diisopropylidene-4,4'-methylenebis(2,6-diethylbenzeneamine), N,N'-di-sec-butylidene-4,4'-methylenebis(2,6-diethylbenzeneamine), N,N'-di(benzylidene)-4,4'-methylenebis(2,6-diethylbenzeneamine), N,N'-di(2-heptylidene)-4,4'-methylenebis(2,6-diisopropylbenzeneamine), N,N'-dicyclobutylidene-4,4'-methylenebis(2-isopropyl-6-methylbenzeneamine), N,N'-di(3-methyl-2-cyclohexenylidene)-4,4'-methylenebis(2-methyl-6-tert-butylbenzeneamine), N,N'-di-sec-butylidene-4,4'-(1,2-ethanediyl)bis(2,6-diethylbenzeneamine), N,N'-di(1-cyclopentylethylidene)-4,4'-(1,2-ethanediyl)bis(2,6-diethylbenzeneamine), N,N'-di(1-phenyl-2-butylidene)-4,4'-(1,2-ethanediyl)bis(2,6-diisopropylbenzeneamine), N,N'-di(2-phenylethylidene)-2,2'-methylenebis(3,4,6-tripentylbenzeneamine), N,N'-di(4-heptylidene)-3,3'-methylenebis(2,5,6-trihexylbenzeneamine), N,N'-dicyclohexylidene-4,4'-methylenebis(2,3,6-trimethylbenzeneamine), N,N'-di(1-cyclobutylethylidene)-4,4'-methylenebis(2,3,4,6-tetramethylbenzeneamine), and the like. Particularly preferred aromatic diimines in which one imino group is on each of two benzene rings are N,N'-diisopropylidene-4,4'-methylenebis(2,6-diethylbenzeneamine) and N,N'-di-sec-butylidene-4,4'-methylenebis(2,6-diethylbenzeneamine).

B. Aromatic Secondary Diamines

An aromatic secondary diamine which is a composition of the invention is a secondary diamine in which each amino hydrocarbyl group has at least two carbon atoms, and which secondary diamine either is in the form of one benzene ring having two secondary amino groups on the ring, which secondary amino groups are meta or para relative to each other, and in which each position ortho (immediately adjacent) to a secondary amino group (—NHR) bears a hydrocarbyl group, or is in the form of two benzene rings connected by an alkylene bridge and having one secondary amino group on each ring, and in which each position ortho (immediately adjacent)

to a secondary amino group bears a hydrocarbyl group. The hydrocarbyl groups ortho to the secondary amino groups on the benzene rings may be the same or different. Examples of suitable hydrocarbyl groups on the benzene ring include methyl, ethyl, propyl, isopropyl, n-butyl, sec-butyl, t-butyl, pentyl, cyclopentyl, hexyl, methylcyclohexyl, heptyl, octyl, cyclooctyl, nonyl, decyl, dodecyl, phenyl, benzyl, and the like. When the aromatic secondary diamine is in the form of two benzene rings connected by an alkylene bridge and having one secondary amino group on each ring and the secondary amino group is adjacent (ortho) to the alkylene bridge, the alkylene bridge is considered as a hydrocarbyl group ortho to the secondary amino group. Preferred hydrocarbyl groups on the benzene rings (ortho to a secondary amino group) of the aromatic secondary diamines are straight chain or branched chain alkyl groups having from one to about six carbon atoms; particularly preferred hydrocarbyl groups are methyl, ethyl, isopropyl, butyl, and mixtures of two or more of these groups. Here, the preference for butyl groups includes n-butyl, sec-butyl, and t-butyl groups. The alkylene bridge of the two-benzene-ring secondary diamine has from one to about six carbon atoms; preferably, the alkylene bridge has from one to about three carbon atoms. More preferably, the alkylene bridge has one or two carbon atoms; highly preferred is an alkylene bridge having one carbon atom, i.e., a methylene group. Particularly preferred amino hydrocarbyl groups are isopropyl and sec-butyl groups.

Throughout this document, the term "amino hydrocarbyl group" refers to the hydrocarbyl group bound to a nitrogen atom of the aromatic secondary diamine which hydrocarbyl group is not the benzene ring to which the nitrogen atom is bound in order to form the aromatic secondary diamine.

The amino hydrocarbyl groups of the aromatic secondary diamine generally have from two to about twenty carbon atoms; the amino hydrocarbyl group may be aliphatic (straight chain, branched, or cyclic) or aromatic. Preferably, the amino hydrocarbyl groups are straight chain or branched chain alkyl groups having from three to about six carbon atoms. Examples of suitable amino hydrocarbyl groups include ethyl, propyl, isopropyl, 1-cyclopropylethyl, n-butyl, sec-butyl, cyclobutyl, 2-ethylbutyl, 3,3-dimethyl-2-butyl, 3-pentyl, 3-penten-2-yl, cyclopentyl, 2,5-dimethylcyclopentyl, 2-cyclopentenyl, hexyl, methylcyclohexyl, menthyl, ionyl, phoryl, isophoryl, heptyl, 2,6-dimethyl-3-heptyl, cyclooctyl, 5-nonyl, decyl, 10-undecenyl, dodecyl, benzyl, 2,4-dimethylbenzyl, 2-phenylethyl, 1-phenylpentyl, 1-naphthyl, 2-naphthyl, 1-naphthylethyl, and the like. Particularly preferred amino hydrocarbyl groups are isopropyl and sec-butyl.

Aromatic secondary diamines with two secondary amino groups on one benzene ring preferably have the secondary amino groups meta relative to each other. In such preferred aromatic secondary diamines, the amino hydrocarbyl group preferably is a straight chain or branched chain alkyl group having from three to about six carbon atoms. Particularly preferred are aromatic secondary diamines in which the hydrocarbyl group between the two meta secondary amino groups is a methyl group, while the two remaining hydrocarbyl groups are ethyl groups, and those in which the hydrocarbyl group between the two meta secondary amino groups is an ethyl group, while one of the two remaining hydrocarbyl groups is a methyl group and the other is an ethyl group, and mixtures thereof, especially when the amino hydrocarbyl groups are isopropyl or sec-butyl groups.

Preferred aromatic secondary diamines in which one secondary amino group is on each of two benzene rings, where the two benzene rings are connected via an alkylene bridge, have both secondary amino groups para relative to the alkylene bridge. A particularly preferred aromatic secondary diamine of this type is a compound where each hydrocarbyl group ortho to a secondary amino group is an ethyl group and the alkylene bridge is a methylene group; this is especially preferred when the amino hydrocarbyl groups are isopropyl or sec-butyl groups.

Aromatic secondary diamines of this invention having both secondary amino groups on one benzene ring include, but are not limited to, N,N'-diisopropyl-2,4,6-triethyl-1,3-benzenediamine, N,N'-di-sec-butyl-2,4,6-triethyl-1,3-benzenediamine, N,N'-di-2-pentyl-2,4,6-triethyl-1,3-benzenediamine, N,N'-diisopropyl-(2,4-diethyl-6-methyl-1,3-benzenediamine), N,N'-di-sec-butyl-(2,4-diethyl-6-methyl-1,3-benzenediamine), N,N'-diisopropyl-(4,6-diethyl-2-methyl-1,3-benzenediamine), N,N'-di-sec-butyl-(4,6-diethyl-2-methyl-1,3-benzenediamine), N,N'-di(2-naphthyl)-(4,6-diethyl-2-methyl-1,3-benzenediamine), N,N'-di(2-cyclopentenyl)-(2,4-diisopropyl-6-methyl-1,3-benzenediamine), N,N'-diisopropyl-(2-methyl-4,6-di-sec-butyl-1,3-benzenediamine), N,N'-di-sec-butyl-(2-methyl-4,6-di-sec-butyl-1,3-benzenediamine), N,N'-di(1-cyclopropylethyl)-(2-methyl-4,6-di-sec-butyl-1,3-benzenediamine), N,N'-di(3,3-dimethyl-2-butyl)-(2-ethyl-4-isopropyl-6-methyl-1,3-benzenediamine), N,N'-diisopropyl-2,4,5,6-tetra-n-propyl-1,3-benzenediamine, N,N'-di(3-penten-2-yl)-2,4,5,6-tetra-n-propyl-1,3-benzenediamine, and N,N'-di(4-hexyl)-2,3,5,6-tetraethyl-1,4-benzenediamine. Particularly preferred aromatic diamines having both amino groups on one benzene ring are N,N'-diisopropyl-(2,4-diethyl-6-methyl-1,3-benzenediamine), N,N'-diisopropyl-(4,6-diethyl-2-methyl-1,3-benzenediamine), and mixtures thereof; N,N'-di-sec-butyl-(2,4-diethyl-6-methyl-1,3-benzenediamine), N,N'-di-sec-butyl-(4,6-diethyl-2-methyl-1,3-benzenediamine), and mixtures thereof.

Examples of aromatic secondary diamines of the invention in which one secondary amino group is on each of two benzene rings include N,N'-diisopropyl-2,2'-methylenebis(6-n-propylbenzeneamine), N,N'-di-sec-butyl-2,2'-methylenebis(3,6-di-n-propylbenzeneamine), N,N'-di(2,4-dimethylbenzyl)-2,2'-methylenebis(5,6-dihexylbenzeneamine), N,N'-diisopropyl-3,3'-methylenebis(2,6-di-n-butylbenzeneamine), N,N'-di(2,4-dimethyl-3-pentyl)-3,3'-methylenebis(2,6-di-n-butylbenzeneamine), N,N'-diisopropyl-4,4'-methylenebis(2,6-diethylbenzeneamine), N,N'-di-sec-butyl-4,4'-methylenebis(2,6-diethylbenzeneamine), N,N'-di(2-hexyl)-4,4'-methylenebis(2,6-diethylbenzeneamine), N,N'-di(1-naphthylethyl)-4,4'-methylenebis(2,6-diisopropylbenzeneamine), N,N'-dicyclobutyl-4,4'-methylenebis(2-isopropyl-6-methylbenzeneamine), N,N'-di(1-penten-3-yl)-4,4'-methylenebis(2-methyl-6-tert-butylbenzeneamine), N,N'-di-sec-butyl-4,4'-(1,2-ethanediyl)bis(2,6-diethylbenzeneamine), N,N'-di(1-cyclopentylethyl)-4,4'-(1,2-ethanediyl)bis(2,6-diethylbenzeneamine), N,N'-di(2-ethylbutyl)-4,4'-(1,2-ethanediyl)bis(2,6-diisopropylbenzeneamine), N,N'-di(10-undecenyl)-2,2'-methylenebis(3,4,6-tripentylbenzeneamine), N,N'-di(4-heptyl)-3,3'-methylenebis(2,5,6-trihexylbenzeneamine), N,N'-dimenthyl-4,4'-methylenebis(2,3,6-trimethylbenzeneamine), N,N'-dibenzyl-4,4'-methylenebis(2,3,4,6-tetramethylbenzeneamine), and the like. Particularly preferred aromatic diamines in which one amino group is on each of two benzene rings are N,N'-diisopropyl-4,4'-methylenebis(2,6-diethylbenzeneamine) and N,N'-di-sec-butyl-4,4'-methylenebis(2,6-diethylbenzeneamine).

Components of the Processes of the Invention

A. Ketones and Aldehydes

In the processes of the invention, hydrocarbyl ketones and hydrocarbyl aldehydes are used. The hydrocarbyl portion of the ketone or aldehyde may be aliphatic (cyclic, branched, or straight chain), unsaturated, aromatic, or alkylaromatic. The hydrocarbyl portion is preferably aliphatic, alkylaromatic, or aromatic. More preferably, the hydrocarbyl portion of the aldehyde or ketone is an aliphatic straight chain or a branched aliphatic group; especially preferred is an aliphatic straight chain. Regarding ketones, this preference for an aliphatic straight chain refers to the hydrocarbyl portions on both sides of the carbonyl group. Preferably, the ketones and aldehydes used in the practice of this invention have from three to about twenty carbon atoms. More preferred are ketones and aldehydes having from three to about fifteen carbon atoms. Especially preferred ketones and aldehydes have a hydrocarbyl portion which is an aliphatic straight chain or a branched aliphatic group, and have from three to about fifteen carbon atoms.

The mole ratio of the ketone or aldehyde to the primary diamine is normally at least about one mole of ketone or aldehyde per mole of amino group, i.e., at least about two moles of ketone or aldehyde per mole of diamine. Preferably, an excess of the ketone or aldehyde is used, more preferably at least about a 10% molar excess of ketone or aldehyde relative to the primary diamine is used. Large excesses of ketone or aldehyde are acceptable in the practice of the invention; the ketone or aldehyde can be, and preferably is, present in enough quantity to also act as a solvent. In fact, a large excess of ketone or aldehyde is considered beneficial because, as is well known in the art, the formation of a diimine behaves as an equilibrium, and excess ketone or aldehyde helps shift the equilibrium to favor diimine formation.

Suitable ketones include acetone (2-propanone), methyl ethyl ketone (2-butanone), 2-pentanone, 3-pentanone, 2-hexanone, 3-hexanone, 2-heptanone, 4-heptanone, 3-octanone, 4-octanone, 3-nonanone, 5-nonanone, 2-undecanone, 6-undecanone, di-n-hexyl ketone, 8-pentadecanone, 9-heptadecanone, 10-nonadecanone, cyclobutanone, cyclopentanone, cyclohexanone, cyclopropyl methyl ketone (1-(cyclopropyl)ethanone), cyclobutyl methyl ketone, cyclopentyl methyl ketone, cyclohexyl methyl ketone, 3-methyl-2-pentanone, 4-methyl-2-pentanone (methyl isobutyl ketone), 2-methyl-cyclopentanone, 3-methyl-cyclopentanone, 5-methyl-2-hexanone, 4-methyl-3-heptanone, 3,3-dimethyl-2-butanone (methyl tert-butyl ketone), 2,4-dimethyl-3-pentanone, 2,6-dimethyl-3-heptanone, 3,5-dimethyl-4-heptanone, 2-methyl-cyclohexanone, 2,5-dimethylcyclopentanone, menthone, ethyl vinyl ketone (1-penten-3-one), 3-penten-2-one, 2-cyclopentenone, α-ionone, β-ionone, phorone (2,6-dimethyl-2,5-heptadien-4-one), isophorone, 1,3-diphenylacetone, phenylacetone (phenyl-2-propanone), 1-phenyl-2-butanone, acetophenone, isobutyrophenone, valerophenone (1-phenyl-1-pentanone), hexanophenone, 1-acetonaphthone, and the like. Preferred ketones include acetone, methyl ethyl ketone, 3,3-dimethyl-2-butanone, 4-methyl-2-pentanone, cyclohexanone, 4-heptanone, and 5-nonanone. Acetone, methyl ethyl ketone, 4-heptanone, 3,3-dimethyl-2-butanone, and 4-methyl-2-pentanone are particularly preferred ketones in the practice of this invention.

Aldehydes that can be used in the practice of this invention include acetaldehyde, propionaldehyde, butyraldehyde, valeraldehyde (pentanal), isovaleraldehyde, hexanal, cyclohexanecarboxaldehyde, heptaldehyde, octyl aldehyde, nonyl aldehyde, decyl aldehyde, undecyl aldehyde, dodecyl aldehyde, 2-ethylbutyraldehyde, crotonaldehyde, undecylenic aldehyde (10-undecenal), cinnamaldehyde, phenylacetaldehyde, benzaldehyde, 2,4-dimethylbenzaldehyde, tolualdehyde, mesitaldehyde, 1-naphthaldehyde, and the like. Preferred aldehydes include acetaldehyde and propionaldehyde.

While the use of either one ketone or one aldehyde is preferred, mixtures may be employed. Such mixtures can include two or more ketones, two or more aldehydes, or at least one ketone and at least one aldehyde. The use of a mixture of ketones and/or aldehydes may result in a mixture of products.

Usually, the ketone and/or aldehyde is in liquid form when it is used in the processes of the invention. For some ketones and aldehydes, elevated temperatures and/or increased pressure will liquefy the ketone or aldehyde. If such conditions are not used, a solvent may be used to provide the ketone or aldehyde in liquid form.

B. Acid Ion Exchange Resins

It is known in the art that strong acids such as $H_2SO_4$ often cause aliphatic ketones to dimerize and/or polymerize. Thus, a feature of this invention is the use of an acid ion exchange resin as the acid catalyst for the formation of the diimines of the invention. Acid ion exchange resins are generally polymers containing protic acid functional groups, where the protic acid functional group, at least in theory, can donate a proton. Using an acid ion exchange resin provides the needed acid for the formation of the diimines. Since acid ion exchange resins are usually solids, dimerization and polymerization of the ketone is minimized. In addition, acid ion exchange resins do not add significant amounts of water to the system, another advantage, because water, especially in large amounts, can shift the equilibrium toward the ketone and primary diamine. Additionally, acid ion exchange resins can be dried to remove water present in the resin, and acid ion exchange resins can be recycled. A particularly preferred acid ion exchange resin is sulfonated divinylbenzene/styrene copolymer, in H ion form, sold as Amberlyst-15 (Rohm and Haas Company), in which the protic acid functional group is —$SO_3H$. In the processes of the invention where it is used, the acid ion exchange resin is typically present in amounts of about 1 wt % to about 10 wt % relative to the primary diamine. Preferably, about 3 wt % to about 7 wt % acid ion exchange resin is used relative to the primary diamine.

C. Hydrogenation Agents

Various hydrogenation agents can be used in the processes of the invention. Which hydrogenation agents are suitable depends on the primary diamine used in the process. Types of hydrogenation agents that can be used include hydride transfer agents such as sodium cyanoborohydride, sodium borohydride, sodium aluminum hydride, lithium aluminum hydride, and the like; "dissolving metal" reagents such as Al with alcohol, Al/Hg, Al/Pd with HCl, Na with alcohol, Na/Hg, Mg with alcohol, Fe with HCl, Zn with HCl, Zn/Cu with HCl, Zn/Hg with HCl, Zn/Pd with HCl, Zn/Cu/Pd with HCl, and the like; borane reductants including $BH_3$-pyridine and $BH_3$-dimethylamine; and hydrogen with a hydrogenation catalyst, where the hydrogenation catalyst can be sulfided platinum on carbon, sulfided palladium on carbon, or a mixture of both of these. All of these hydrogenation agents are normally suitable for processes of the invention in which the primary diamine is an aliphatic diamine or an aromatic primary diamine in which at least one position ortho to each primary amino group has a hydrogen atom as a substituent (see below). A preferred type of hydrogenation agent is hydrogen with a hydrogenation catalyst; an especially preferred hydrogenation catalyst is sulfided platinum on carbon.

Some of the just-described hydrogenation agents do not seem to be as effective when the primary diamine is an aromatic primary diamine in which each position ortho to a primary amino group bears a hydrocarbyl group (see below). In particular, hydride transfer agents react very slowly with aromatic primary diamines in which each position ortho to a primary amino group bears a hydrocarbyl group, sometimes forming gels; in addition, to date, palladium on carbon and platinum on carbon (unsulfided, or without a strong acid present) have not yielded observable products when used with an aromatic primary diamine in which each position ortho to a primary amino group bears a hydrocarbyl group. Palladium on carbon and platinum on carbon can be effective hydrogenation catalysts in the presence of hydrogen sulfide or a strong acid such as sulfuric acid, hydrochloric acid, phosphoric acid, and the like, for processes using aromatic primary diamines in which each position ortho to a primary amino group bears a hydrocarbyl group. Thus, for aromatic primary diamines in which each position ortho to a primary amino group bears a hydrocarbyl group, the hydrogenation agent is generally either a dissolving metal reagent or hydrogen with a hydrogenation catalyst, where the hydrogenation catalyst is sulfided platinum on carbon, sulfided palladium on carbon, or a mixture thereof, or is selected from palladium on carbon, platinum on carbon, and a mixture of both of these, when used with hydrogen sulfide or at least one strong acid. In the practice of this invention, sulfided platinum on carbon, Pt(S)/C, has been found to be a particularly effective hydrogenation catalyst for aromatic primary diamines in which each position ortho to an amino group bears a hydrocarbyl group; thus hydrogen with sulfided platinum on carbon is an especially preferred hydrogenation agent for processes employing aromatic primary diamines in which each position ortho to a primary amino group bears a hydrocarbyl group.

Suitable amounts of hydrogenation catalyst can be relatively low, i.e., in the range of about 0.5 wt % to about 10 wt % relative to the primary diamine. More suitably, in the range of about 0.75 wt % to about 6 wt % hydrogenation catalyst can be used relative to the primary diamine. It has now been found that with the use of greater amounts of the hydrogenation catalyst, the reaction occurs more quickly. Thus, a weight ratio of primary diamine to catalyst in the range of about 20:1 to about 1:20 is feasible, and a weight ratio of primary diamine to hydrogenation catalyst in the range of about 10:1 to about 1:10 is preferred. More preferred is a weight ratio of primary diamine to hydrogenation catalyst in the range of about 1:1 to about 1:5. The use of an amount of catalyst in the preferred ranges provides secondary diamines in high yields in relatively short reaction times, in at least some instances in less than half an hour or in several minutes on the laboratory timescale.

The hydrogenation catalyst an be in either powdered form or in granular form. The granular form of the hydrogenation catalyst settles out of solution more readily than does the powdered form, and the granular form tends to have slower reaction rates than are seen with powdered form. However, side reactions are minimized when the hydrogenation catalyst is in granular form. Thus, the preferable form for the hydrogenation catalyst may vary with the particular primary diamine and ketone or aldehyde chosen, as minimizing side reactions can be of greater significance in some systems, while in others the increased reaction rate can be more important.

When choosing a hydrogenation agent, especially the "dissolving metal" reagents which are used in conjunction with acid, and hydrogen with a hydrogenation catalyst where acid will be present, it should be remembered that, as mentioned above, strong acids can cause dimerization and/or polymerization of some ketones.

D. Aromatic Primary Diamines

One type of aromatic primary diamine used in the processes of the invention has at least one position ortho to each primary amino group which has a hydrogen atom as a substituent, and the aromatic primary diamine is either in the form of one benzene ring having two primary amino groups on the ring, or in the form of two benzene rings connected by an alkylene bridge and having one primary amino group on each ring. The benzene rings may have, but need not have, one or more hydrocarbyl groups on the benzene ring(s). Hydrocarbyl groups, when present on the benzene rings, may be the same or different. When both primary amino groups are on one benzene ring, the primary amino groups may be in any position relative to each other on the ring; preferably, the primary amino groups are meta or para relative to each other. When the primary amino groups are on two benzene rings connected by an alkylene bridge, they may be in any position on the rings; preferably, each primary amino group is meta or para relative to the alkylene bridge. The alkylene bridge of the two-benzene-ring diamine has from one to about six carbon atoms; preferably, the alkylene bridge has from one to about three carbon atoms. More preferably, the alkylene bridge has one or two carbon atoms; highly preferred is an alkylene bridge having one carbon atom. The hydrocarbyl groups, when present on the benzene ring(s), are as described above for the aromatic diimines. When one or more hydrocarbyl groups are present on the benzene ring(s), the hydrocarbyl groups can have from one to about twenty carbon atoms; preferably, the hydrocarbyl groups have from one to about six carbon atoms.

Suitable aromatic primary diamines having both primary amino groups on one benzene ring include, but are not limited to, 1,2-benzenediamine, 1,3-benzenediamine, 1,4-benzenediamine, 4-ethyl-1,2-benzenediamine, 2-isopropyl-1,3-benzenediamine, 4-tert-butyl-1,3-benzenediamine, 2-pentyl-1,4-benzenediamine, 4,5-dihexyl-1,2-benzenediamine, 4-methyl-5-heptyl-1,3-benzenediamine, 4,6-di-n-propyl-1,3-benzenediamine, 2,5-dioctyl-1,4-benzenediamine, 2,3-diethyl-1,4-benzenediamine, and 4,5,6-trihexyl-1,3-benzenediamine. Preferred aromatic primary diamines having both primary amino groups on one benzene ring and at least one position ortho to each primary amino group has a hydrogen atom as a substituent include 1,3-benzenediamine and 1,4-benzenediamine.

Examples of suitable aromatic primary diamines in which one primary amino group is on each of two benzene rings include 2,2'-methylenebis(benzeneamine), 2,3'-methylenebis-(benzeneamine), 2,4'-methylenebis(benzeneamine), 3,3'-methylenebis(benzeneamine), 3,4'-methylenebis(benzeneamine), 4,4'-methylenebis(benzeneamine), 4,4'-(1,2-ethanediyl)bis-(benzeneamine), 3,4'-(1,3-propanediyl)bis (benzeneamine), 2,2'-methylenebis(5-tert-butylbenzeneamine), 3,3'-methylenebis(2-methylbenzeneamine), 3,3'-methylenebis(5-pentylbenzeneamine), 3,3'-methylenebis(6-isopropylbenzeneamine), 4,4'-methylenebis(2-methylbenzeneamine), 4,4'-methylenebis(3-sec-butylbenzeneamine), 4,4'-(1,2-ethanediyl)bis(2-methylbenzeneamine), 3,3'-methylenebis(2,4-dipentylbenzeneamine), 3,3'-methylenebis(5,6-diisopropylbenzeneamine), 4,4'-methylenebis(2, 3-di-sec-butylbenzeneamine), 4,4'-methylenebis(3,5-di-tert-butylbenzeneamine), and the like. Preferred aromatic primary diamines in which one primary amino group is on each of two benzene rings and at least one position ortho to each primary amino group has a hydrogen atom as a substituent include 4,4'-methylenebis(benzeneamine) and 4,4'-methylenebis(2-methylbenzeneamine).

E. Preferred Aromatic Primary Diamines

Another type of aromatic primary diamine for use in the processes of the invention, which is a preferred type of aromatic primary diamine, is an aromatic primary diamine in which each position ortho (immediately adjacent) to a primary amino group bears a hydrocarbyl group, and which aromatic primary diamine either is in the form of one benzene ring having two primary amino groups on the ring, which primary amino groups are meta or para relative to each other, or is in the form of two benzene rings connected by an alkylene bridge and having one primary amino group on each ring. The hydrocarbyl groups on the benzene rings (adjacent to the amino groups) generally have up to about twenty carbon atoms, and the hydrocarbyl groups may be the same or different. The alkylene bridge of the two-benzene-ring primary diamine has from one to about six carbon atoms; preferably, the bridge has from one to about three carbon atoms. More preferably, the alkylene bridge has one or two carbon atoms; especially preferred as the alkylene bridge is a methylene group. Particularly preferred hydrocarbyl groups on the benzene ring(s) are methyl, ethyl, isopropyl, butyl, and mixtures of two or more of these groups. Here, butyl groups include n-butyl, sec-butyl, and t-butyl groups.

More preferred aromatic primary diamines with two primary amino groups on one benzene ring have the primary amino groups meta relative to each other. In these more preferred aromatic primary diamines, the amino hydrocarbyl group preferably is a straight-chain or branched-chain alkyl group having from one to about six carbon atoms. Highly preferred hydrocarbyl groups are methyl, ethyl, isopropyl, butyl, and mixtures of two or more of these groups, where the preference for butyl groups includes n-butyl, sec-butyl, and t-butyl groups. Particularly preferred are aromatic primary diamines in which the hydrocarbyl group between the two meta primary amino groups is a methyl group, while the two remaining hydrocarbyl groups are ethyl groups, and those in which the hydrocarbyl group between the two meta primary amino groups is an ethyl group, while one of the two remaining hydrocarbyl groups is a methyl group and the other is an ethyl group, and mixtures thereof. More preferred aromatic primary diamines are also those in which one primary amino group is on each of two benzene rings, where the two benzene rings are connected via an alkylene bridge, and have both primary amino groups para relative to the alkylene bridge. An especially preferred aromatic primary diamine of this type is a compound where each hydrocarbyl group ortho to a primary amino group is an ethyl group and the alkylene bridge is a methylene group. Examples of more preferred aromatic primary diamines include 3,6-di-n-butyl-1,2-benzenediamine, 2,4,6-triethyl-1,3-benzenediamine, 2,4-diethyl-6-methyl-1,3-benzenediamine, 4,6-diethyl-2-methyl-1,3-benzenediamine, 2,4-diisopropyl-6-methyl-1,3-benzenediamine, 2-methyl-4,6-di-sec-butyl-1,3-benzenediamine, 2-ethyl-4-isopropyl-6-methyl-1,3-benzenediamine, 2,3,5-tri-n-propyl-1,4-benzenediamine, 2,3-diethyl-5-sec-butyl-1,4-benzenediamine, 3,4-dimethyl-5,6-diheptyl-1,2-benzenediamine, 2,4,5,6-tetra-n-propyl-1,3-benzenediamine, 2,3,5,6-tetraethyl-1,4-benzenediamine, 2,2'-methylenebis(6-n-propylbenzeneamine), 2,2'-methylenebis(3,6-di-n-propylbenzeneamine), 3,3'-methylenebis(2,6-di-n-butylbenzeneamine), 4,4'-methylenebis(2,6-diethylbenzeneamine), 4,4'-methylenebis(2,6-diisopropylbenzeneamine), 4,4'-methylenebis(2-isopropyl-6-methylbenzeneamine), 4,4'-(1,2-ethanediyl)bis(2,6-diethylbenzeneamine), 4,4'-(1,2-ethanediyl)bis(2,6-diisopropylbenzeneamine), 2,2'-methylenebis(3,4,6-tripentylbenzeneamine), 3,3'-methylenebis(2,5,6-trihexylbenzeneamine), 4,4'-methylenebis(2,3,6-trimethylbenzeneamine), 4,4'-methylenebis(2,3,4,6-tetramethylbenzeneamine), and the like. Of these more preferred types of aromatic primary diamines, particularly preferred are 4,4'-methylenebis(2,6-diethylbenzeneamine), 4,4'-methylenebis(2,6-diisopropylbenzeneamine), and a mixture of 2,4-diethyl-6-methyl-1,3-benzenediamine and 4,6-diethyl-2-methyl-1,3-benzenediamine (DETDA). Throughout this document, when the term "more preferred aromatic primary diamine" is used, it is meant to refer to aromatic primary diamines of the type described in this paragraph. The use of more preferred aromatic primary diamines in the processes of the present invention produce compositions of the invention.

F. Aliphatic Primary Diamines

The aliphatic primary diamines used in the processes of this invention are hydrocarbyl primary diamines where the hydrocarbyl portion of the diamine is aliphatic. The hydrocarbyl portion of the aliphatic diamine can be cyclic, branched, or straight chain. Preferably, the aliphatic primary diamine has about two to about twenty carbon atoms; more preferably, the aliphatic primary diamine has about four to about ten carbon atoms. Particularly preferred aliphatic diamines have cyclic or straight chain hydrocarbyl portions and have about four to about ten carbon atoms. Suitable aliphatic primary diamines include, but are not limited to, ethylenediamine, 1,2-diaminopropane, 1,3-diaminopropane, 1,4-diaminobutane, 1,5-diaminopentane, 1,5-diamino-2-methylpentane, 1,6-diaminohexane, 2,5-dimethyl-2,5-hexanediamine, 1,2-diaminocyclohexane, 1,3-diaminocyclohexane, 1,4-diaminocyclohexane, 2,4-diethyl-6-methyl-1,3-cyclohexanediamine, 4,6-diethyl-2-methyl-1,3-cyclohexanediamine, 1,3-cyclohexanebis(methylamine), 1,4-cyclohexanebis(methylamine), isophorone diamine, bis(p-aminocyclohexyl)methane, bis(3-methyl-4-aminocyclohexyl)-methane, 1,8-diamino-p-menthane, 1,7-diaminoheptane, 1,8-diaminooctane, 1,10-diaminodecane, 1,12-diaminododecane, and 3(4),8(9)-bis-(aminomethyl)-tricyclo[5.2.1.0(2,6)]decane (TCD diamine; also called octahydro-4,7-methanoinden-1(2),5(6)-dimethanamine or octahydro-4,7-methano-1H-indenedimethyl-amine). Preferred aliphatic primary diamines include isophorone diamine, 1,6-diaminohexane, 1,8-diaminooctane, and TCD diamine. Particularly preferred combinations in the processes of this invention are the use of isophorone diamine with 5-nonanone, the use of isophorone diamine with 4-heptanone, the use of isophorone diamine with cyclohexanone, the use of isophorone diamine with 4-methyl-2-pentanone, the use of isophorone diamine with 3,3-dimethyl-2-butanone, the use of 1,6-diaminohexane with 3,3-dimethyl-2-butanone, and the use of TCD diamine with 3,3-dimethyl-2-butanone.

G. Solvents

It is often preferred to use a large enough excess of ketone or aldehyde such that the ketone or aldehyde serves as the solvent in the processes of the invention; however, one or more solvents can be present during the processes of the invention. For processes where an acid ion exchange resin is present, the inclusion of solvent is generally considered unnecessary. Solvents that can be used in processes where an acid ion exchange resin is present include, but are not limited to, liquid aromatic hydrocarbons, liquid aliphatic hydrocarbons, liquid halogenated aliphatic hydrocarbons, ethers, esters, alcohols, and mixtures of two or more solvents. For processes in which a hydrogenation agent is present, the presence of a solvent is not required, but inclusion of a solvent is recommended and preferred. While the processes will make the desired product in the absence of solvent, the resultant mixture is frequently a very thick, viscous mixture which is often difficult to process further. The important consideration in selecting a solvent is that it not interfere with the functioning of the chosen hydrogenation agent; for example, the solvent chosen should not poison the hydrogenation catalyst. Solvent types that can be used when a hydrogenation agent is present include, but are not limited to, liquid aromatic hydrocarbons, liquid aliphatic hydrocarbons, liquid halogenated aliphatic hydrocarbons, ethers, esters, alcohols, and a mixture of two or more solvents. When both an acid ion exchange resin and a hydrogenation agent are present in the same process, solvents that are compatible with both are selected.

Suitable liquid hydrocarbons include benzene, toluene, xylenes, mesitylene, cumene, cymene, pentane, hexane, isohexane, cyclohexane, methylcyclohexane, heptane, octane, cyclooctane, nonane, and the like. Examples of liquid halogenated aliphatic hydrocarbons that can be used include dichloromethane, trichloromethane, 1,2-dichloroethane, 1-bromo-2-chloroethane,(chloromethyl)cyclopropane, 1-bromobutane, cyclobutyl chloride, neopentyl chloride, 1-bromo-5-chloropentane, cyclopentyl bromide, 1,6-dibromohexane, trans-1,2-dichlorocyclohexane, 1-chloroheptane, 1,8-dichlorooctane, and the like. Ethers that are suitable for use in this invention include diethyl ether, di-n-propyl ether, diisopropyl ether, di-n-butyl ether, butyl ethyl ether, cyclohexylmethyl ether, tetrahydrofuran, 1,3-dioxane, 1,3-dioxolane, glyme (the dimethyl ether of ethylene glycol), 2-methoxyethyl ether (diglyme), and the like. Examples of esters that can be used include ethyl acetate, isopropyl acetate, n-butyl acetate, isobutyl acetate, tert-butyl acetate, n-amyl acetate, isoamyl acetate, hexyl acetate, methyl propionate, ethyl propionate, ethyl butyrate, and the like. Alcohols that can be used in the practice of the invention include methanol, ethanol, 1-propanol, 2-propanol, 1-butanol, 2-methyl-1-propanol, 1-methyl-1-propanol, cyclopropylmethanol, cyclobutanol, cyclopentanol, cis-2-methylcyclohexanol, and the like. Preferred solvents when a hydrogenation agent is present include dichloromethane, ethyl acetate, and toluene.

H. Water Removal Agents

As described below, the presence of large amounts of water in the processes of the invention is usually not desirable. Without wishing to be bound by theory, it is believed that the presence of large amounts of water causes hydrolysis of the diimines. However, it has now been found that the presence of water may be less detrimental than previously believed in the processes of the invention, or at least in the processes of the invention which employ hydrogen and a hydrogenation catalyst, particularly when two phases can be formed in the reaction product mixture (e.g., an aqueous phase and an organic phase).

One method for minimizing the amount of water in the reaction mixture is to use a water removal agent. A water removal agent may be included in the reaction mixture to remove water as the water is produced in the process. The only requirement is that the water removal agent not adversely affect the reaction or its products. Suitable water removal agents include molecular sieves, silica gel, calcium chloride, and the like. Molecular sieves are a preferred water removal agent in the practice of this invention.

An alternative to the use of a water removal agent is the inclusion of a solvent or enough excess ketone or aldehyde to act as the solvent to effectively dilute the water is recommended and preferred. When a solvent is used, a solvent that is able to azeotrope with water and thereby remove water as it is produced during a process is a preferred way of operating. Particularly preferred solvents that remove water are hexanes and toluene. Another preferred way of operating when using a solvent is to use a solvent which takes water into a phase separate from that in which the reaction is occurring; preferred solvents for this way of operating include toluene and dichloromethane. Both inclusion of a solvent or enough excess ketone or aldehyde to act as the solvent and the use of a water removal agent may be employed to minimize the amount of water. An especially preferred way of operating is to employ enough excess ketone or aldehyde to dilute the water.

Processes of the Invention

Normally, when an aromatic primary diamine is used, the hydrocarbyl groups on the aromatic ring and the placement of the amino groups on the ring(s) of the aromatic diimine and/or the aromatic secondary diamine formed in the processes of the invention correspond to those hydrocarbyl groups and the placement of the amino groups in aromatic primary diamine being used in the process.

Large amounts of water are usually undesired during the processes of the invention because such water shifts the equilibrium toward the ketone or aldehyde and the primary diamine, since water is produced during the formation of a diimine. Without wishing to be bound by theory, in the processes of the invention in which a secondary diamine is prepared from a primary diamine, it is believed that a diimine is formed as an intermediate; therefore, large amounts of water are normally not desired in such processes. However, the presence of water, especially in small amounts, during the processes of the invention is not detrimental. Thus, the use of a solvent that is able to azeotrope with water and thereby remove water as it is produced during a process is a preferred way of operating. Particularly preferred solvents that remove water are hexanes and toluene. Another preferred way of operating is to use a solvent which takes water into a phase separate from that in which the reaction is occurring; preferred solvents for this way of operating include toluene and dichloromethane. The presence of a solvent in a hydrogenation is not required, but inclusion of a solvent or enough excess ketone or aldehyde to act as the solvent is recommended and preferred, because of the viscous nature of the product mixture, as described above under the discussion of solvents.

In the processes of this invention, the presence of oxygen is generally not detrimental. The presence of an inert atmosphere comprised of one or more inert gases, such as, for example, nitrogen, helium, or argon is often preferred, especially during hydrogenations which do not involve hydrogen gas. Operation under a blanket of hydrogen is preferred when the hydrogenation agent is hydrogen and a hydrogenation catalyst.

A. Process for Forming a Diimine Using an Acid Ion Exchange Resin

Diimines, including the aromatic diimines that are compositions of the present invention, can be prepared by mixing together a ketone or an aldehyde and a primary diamine in the presence of an acid ion exchange resin. The order of addition of the ketone, acid ion exchange resin, primary diamine, and optional solvent to the reaction zone for the preparation of the diimine is not considered important. Preferably, the primary diamine and the ketone are mixed together prior to the addition of the acid ion exchange resin and, if used, solvent. Generally, during the preparation of a diimine from a primary diamine in the presence of an acid ion exchange resin, the temperature is kept in the range of about 35° C. to about reflux temperature; preferably, the temperature is such that the mixture is at about reflux temperature. Reaction times on the laboratory scale are on the order of about four hours to about sixty hours.

At least a portion of a diimine formed in this process can be hydrogenated to form a secondary diamine. The diimine can be isolated from the reaction medium in which it was formed prior to the hydrogenation; however, the hydrogenation can be performed successfully without isolating the diimine from the reaction medium in which it was formed.

A secondary diamine can be prepared by mixing together a suitable hydrogenation agent and the diimine. For the hydrogenation of the diimine, it is not necessary to exclude water. Temperatures for the hydrogenation of a diimine to form a secondary diamine are normally in the range of about 20° C. to about 130° C.; preferably, temperatures are in the range of about 20° C. to about 60° C. On the laboratory scale, reaction times are typically about four hours to about twenty hours. When hydrogen and a hydrogenation catalyst are used, the hydrogen gas pressure is preferably in the range of about 14 pounds per square inch (psi) to about 300 psi ($9.65 \times 10^4$ to $2.07 \times 10^6$ Pa); more preferably, the pressure is in the range of about 50 psi to about 150 psi ($3.45 \times 10^5$ to $1.03 \times 10^6$ Pa).

A particularly preferred method for preparing a secondary diamine from a diimine is to place the diimine, hydrogenation catalyst (especially sulfided platinum on carbon) and solvent in a reaction vessel, and then to seal the reaction vessel under hydrogen gas pressure. The vessel is then heated as desired while the reaction mixture is stirred.

B. Process for Forming a Secondary Diamine Using an Acid Ion Exchange Resin and a Hydrogenation Agent Together Secondary diamines can be prepared in one step by mixing together, in the same reaction zone, a ketone or aldehyde, a primary diamine, an acid ion exchange resin, and a hydrogenation agent. Normally, during this one step preparation of a secondary diamine from a primary diamine, the temperature is kept in the range of about 20° C. to about 140° C.; preferably, the temperature is in the range of about 50° C. to about 130° C. More preferably, the temperature is in the range of about 80° C. to about 130° C. When hydrogen and a hydrogenation catalyst are used, the hydrogen gas pressure is preferably in the range of about 14 psi to about 300 psi ($9.65 \times 10^4$ to $2.07 \times 10^6$ Pa); more preferably, the pressure is in the range of about 50 psi to about 150 psi ($3.45 \times 10^5$ to $1.03 \times 10^6$ Pa). Reaction times on the laboratory scale are on the order of about two hours to about eight hours. On the plant scale, reaction times are on the order of about seven hours to about twenty-four hours.

C. Process for Forming a Secondary Diamine Using Hydrogen and a Hydrogenation Catalyst Another way to prepare secondary diamines in one step is by mixing together at least one ketone or aldehyde, hydrogen, a hydrogenation catalyst which is sulfided platinum on carbon, sulfided palladium on carbon, or a mixture thereof, and at least one primary diamine. The pressure and temperature conditions for this process vary with the nature of the primary diamine used in the process. As is well known in the art, aliphatic primary diamines generally react more readily in comparison to aromatic primary diamines, and thus gentler conditions can be used with aliphatic diamines, although some aliphatic primary diamines with substituents in close proximity to the amino group may require more forcing conditions. Similarly, it is known that aromatic primary diamines in which at least one position ortho to each amino group has a hydrogen atom as a substituent are more reactive than aromatic primary diamines in which each position ortho to an amino group bears a hydrocarbyl group, and thus more forcing conditions are typically necessary for the aromatic primary diamines in which each position ortho to an amino group bears a hydrocarbyl group. To date, in the practice of the invention, this process has yielded secondary diamines; formation of tertiary diamines has not been observed.

When the primary diamine is an aromatic primary diamine in which at least one position ortho to each amino group has a hydrogen atom as a substituent, the process is conducted at a temperature in the range of about 20° C. to about 120° C. and at a pressure in the range of about 14 to about 125 pounds per square inch ($9.65 \times 10^4$ to $8.62 \times 10^5$ Pa). Preferably, temperatures are in the range of about 20° C. to about 80° C. and pressures are preferably in the range of about 50 to about 125 pounds per square inch ($3.45 \times 10^5$ to $8.62 \times 10^5$ Pa).

When the primary diamine is an aromatic primary diamine in which each position ortho to an amino group bears a hydrocarbyl group (i.e., the primary diamine is a more preferred aromatic primary diamine), the process is conducted at a temperature in the range of about 22° C. to about 140° C. and at a pressure in the range of about 14 to about 150 pounds per square inch ($9.65 \times 10^4$ to $1.03 \times 10^6$ Pa). Preferably, temperatures are in the range of about 50° C. to about 130° C. and pressures are preferably in the range of about 50 to about 125 pounds per square inch ($3.45 \times 10^5$ to $8.62 \times 10^5$ Pa). Temperatures toward the higher end of these ranges are preferred because the reaction rates are usually faster. More particularly, when employing temperatures in the lower end of the range, e.g., in the range of about 22° C. to about 50° C., the process tends to produce a mixture of mono-substituted aromatic diamine and bis-substituted aromatic diamine. As the temperature is increased, e.g., to a temperature in the range of about 50° C. to about 130° C., greater amounts of the bis-substituted aromatic diamine are formed. Here, the term "mono-substituted aromatic diamine" refers to an aromatic diamine in which one amino group is secondary (i.e., substituted) and in which the other amino group remains a primary amino group. Similarly, the term "bis-substituted aromatic diamine" refers to an aromatic diamine in which both amino groups are secondary amino groups.

When the primary diamine is an aliphatic primary diamine, the process is conducted at a temperature in the range of about 20° C. to about 140° C. and at a pressure in the range of about 14 to about 150 pounds per square inch ($9.65 \times 10^4$ to $1.03 \times 10^6$ Pa). Preferably, temperatures are in the range of about 20° C. to about 80° C. and pressures are preferably in the range of about 50 to about 125 pounds per square inch ($3.45 \times 10^5$ to $8.62 \times 10^5$ Pa).

A particularly preferred method for preparing a secondary diamine is to place the primary diamine, hydrogenation catalyst, and solvent in a reaction vessel, and then to seal the reaction vessel under hydrogen gas pressure. The vessel is then heated as desired while the reaction mixture is stirred. On the laboratory scale, reaction times are typically about five hours to about twenty hours.

In another particularly preferred method for preparing a secondary diamine, (i) at least one ketone or aldehyde and at least one primary diamine, these being fed separately and/or in any combination(s), and (ii) hydrogen, are concurrently fed into a reaction zone in which a hydrogenation catalyst is present. The temperature and hydrogen pressure are continuously or substantially continuously maintained during all or substantially all of the time the concurrent feeding is occurring, such that a secondary diamine is formed. This method can be carried out in batch mode, in semi-batch mode, or, preferably, in continuous mode. Normally and preferably, the hydrogenation catalyst is charged to the reaction zone prior to the initiation of the feeds containing the primary diamine, the ketone or aldehyde, and hydrogen. While it is possible to initiate the feeds of ketone or aldehyde and primary diamine prior to initiating the feed of hydrogen, it is recommended and preferred that the hydrogen feed is initiated at the same time or substantially the same time as the feeds of ketone or aldehyde and primary diamine are initiated, because this has been observed to minimize the formation of impurities. Once the concurrent, suitably-proportioned feeds are initiated, product formation normally commences within a few minutes. In a batch operation, the feeds are typically continued until the reactor has been, or until the reactors have been, filled to the desired level. Usually at this point, the feeds are terminated, and the secondary diamine which has formed is separated from the reaction mixture, typically by distillation or recrystallization.

A reaction zone is formed at the place at which the primary diamine, ketone or aldehyde, hydrogen, and the hydrogenation catalyst come into contact. Normally and preferably, the hydrogenation catalyst is placed in the intended reaction zone and the primary diamine, ketone or aldehyde, and hydrogen are fed to the location of the hydrogenation catalyst. Preferably, the primary diamine, ketone or aldehyde, and hydrogen are concurrently fed into a reaction zone composed of at least one reactor in which the primary diamine, ketone or aldehyde, and hydrogen all come together for the first time in the presence of the hydrogenation catalyst. The reaction zone can be a conventional reactor, mixing vessel, pipe, or the like. Examples of suitable reactors include a packed bed reactor and a trickle bed reactor. In a particularly preferred continuous operation, the reaction zone is a tubular reactor of sufficient length and volume for the reaction to occur therein.

The desired temperature and hydrogen pressure are continuously or substantially continuously maintained during all or substantially all of the time the concurrent feeding is occurring, such that a secondary diamine is formed. The hydrogen feed is such that once the hydrogen feed is initiated, the desired hydrogen pressure in the reaction zone is maintained continuously or substantially continuously. The reaction mixture emerging from the reaction zone can be subjected to further steps, such as separation of at least a portion of the secondary diamine product from the reaction mixture. The reaction mixture may be recycled to the reaction zone if desired; preferably, such recycle occurs after at least a portion of the product has been removed from the reaction mixture. Since formation of the secondary diamine is usually rapid, long ride periods are normally unnecessary. The hydrogenation catalyst may become inactive after long periods of use; such inactive catalyst can be, and preferably is, reactivated and reused.

Preferably the concurrent feeds are continuous feeds. It is also preferable that the feeds are at least co-feeds—i.e., at least two feeds are utilized, namely (i) a mixture of the primary diamine and the ketone or aldehyde, and (ii) hydrogen. However, it is highly preferable to conduct a tri-feed process, where the feeds are (i) a primary diamine or a mixture of the primary diamine and the ketone or aldehyde, (ii) hydrogen, and (iii) the ketone or aldehyde. It is also within the scope of this invention to conduct other multi-feed processes. It is possible for example, to have additional feed(s) of e.g., ketone or aldehyde, although such operation offers no particular advantage. In all cases, the feeds are proportioned such that the ketone or aldehyde is present in excess relative to the primary amine in the reaction zone. More preferably, sufficient ketone or aldehyde is present to act as a solvent for the process. It is possible and within the scope of this invention to feed a solvent either alone, or in combination with the primary amine and/or the ketone or aldehyde, or both. However, it is preferred that the ketone or aldehyde be used as the solvent for the process.

When operating in a continuous mode and once the continuous feeds have been initiated, the feeds may be adjusted in fine tuning the operation so as to establish and maintain the desired operating conditions for steady-state operation. Such operation typically can be conducted without mishap for long periods of time before shutdown, e.g., for plant maintenance. To further minimize disruptions in the process, a series of two or more reaction zones may be utilized so that when the hydrogenation catalyst in one reaction zone in no longer active, the feeds of primary diamine, ketone or aldehyde, and hydrogen can be switched to another reaction zone which has active hydrogenation catalyst. Thus, once steady-state conditions have been achieved in a continuous process, the separate feeds can be fed in appropriate proportions on a continuous basis, and the reaction zone maintained under the appropriate reaction conditions for virtually unlimited periods of time. Concurrently, a portion of the reaction mixture is usually and preferably continuously being removed from the reaction zone.

The use of the term "concurrent" does not exclude the possibility of inconsequential interruptions taking place during the feeds. Nor does this term imply that the feeds must start at exactly the same moment in time. In the case of a co-feed process, the two feeds can be initiated with an interval of time between such initiation as long as the interval is sufficiently short as to cause no material adverse effect upon the overall process. Likewise in the case of a tri-feed or multi-feed operation, there may be one or two different time intervals between or among the respective feeds, again provided that the time intervals are of sufficiently short duration to cause no material adverse effect upon the overall process.

An important feature of this process is the concurrent feeding of the separate feeds referred to above. It is again to be emphasized that the term "concurrent" does not imply that the feeds must start at exactly the same time or that they must stop at exactly the same period of time. Rather, the term is used in the sense that during substantially the entire reaction period, the designated feeds are being maintained. It should also be understood that while these concurrent feeds are preferably continuous concurrent feeds, slight interruptions in a feed are acceptable provided that the duration of the interruption is sufficiently small as to cause no material disruption in the reaction. Thus as used herein, the terms "concurrent" and "continuous" should be understood to embrace the minor departures just referred to. Naturally, those skilled in the art will strive to utilize the concurrent feeds with as little non-concurrence as possible. Likewise, those skilled in the art will of course seek to maintain the continuous feeds with as few interruptions as possible under the given circumstances in which the operation is being conducted.

These processes, whether performed in a batch mode, semi-batch mode, or continuous mode, are preferably conducted so that such things as the feeds, reaction, and maintenance of specified temperature and hydrogen pressure occur "continuously" during the reaction. However, it cannot be stressed strongly enough that one must not gain the impression that inconsequential interruption in one or more of such things cannot occur. Interruptions which do not materially affect the conduct of the process are not excluded from the scope of this invention. To safeguard against hypertechnical legalistic word interpretation, it has been deemed prudent to employ terms such as "substantially continuously" in describing this invention. But whatever the terms used, the process should be conducted as one of ordinary skill in the art would carry out the processes after a thorough, unbiased reading of this entire disclosure and in keeping with the spirit of the invention gained from such a reading.

Workup and Recovery from the Processes of the Invention

The diimines produced by the processes of this invention are usually liquids. The diimine can be isolated if desired. Methods for separating liquids that are well known in the art can be employed to separate at least a portion of the diimine from the other components of the reaction mixture. Such methods include, for example, chromatography and distillation. Of course, the diimine need not be isolated from the reaction mixture; instead, the diimine can be further reacted, for example, to form a secondary diamine. The secondary diamines produced by the processes of this invention are usually liquids, and may be isolated as just described for a diimine, or used in non-isolated form. For the secondary diamines, distillation is a preferred separation method. When the diimine or secondary diamine produced is a solid, standard solid-liquid separation methods such as centrifugation, filtration, or recrystallization can be used to separate at least a portion of the product from the liquid portion of the reaction mixture.

It is generally economical to recover and recycle excess ketone or aldehyde, particularly when the ketone or aldehyde is used in enough excess to act as a solvent for the reaction mixture. Separation of the ketone or aldehyde from the reaction mixture can be performed by distillation, with separation of aqueous portions of any azeotropes encountered, or with decantation of the aqueous layer followed by distillation of the ketone or aldehyde layer. Once at least a portion of the product diimine or secondary diamine has been removed from the reaction mixture, unreacted starting materials can be recycled to the reactor to form a portion of the feed stock.

Products of the Processes of the Invention

When a more preferred aromatic primary diamine of the invention (i.e., an aromatic primary diamine which either is in the form of one benzene ring having two primary amino groups on the ring, which primary amino groups are meta or para relative to each other, and in which each position ortho to a primary amino group bears a hydrocarbyl group, or is in the form of two benzene rings connected by an alkylene bridge and having one primary amino group on each ring, and in which each position ortho to a primary amino group bears a hydrocarbyl group) is used, an aromatic diimine or an aromatic secondary diamine corresponding to an aromatic diimine or an aromatic secondary diamine listed above as a composition of the invention is produced.

A. Aromatic Diimines

Aromatic diimines which are not compositions of the present invention that can be produced by the processes of the invention include, but are not limited to, N,N'-diisopropylidene-1,2-benzenediamine, N,N'-di-sec-butylidene-1,3-benzenediamine, N,N'-di(3-hexylidene)-1,4-benzenediamine, N,N'-dicyclopentylidene-4-ethyl-1,2-benzenediamine, N,N'-di-sec-butylidene-(4-tert-butyl-1,3-benzenediamine), N,N'-di(1-cyclopropylethylidene)-2-pentyl-1,4-benzenediamine, N,N'-di(undecylidene)-(4-methyl-5-heptyl-1,3-benzenediamine), N,N'-di(2-cyclopentenylidene)-4,6-di-n-propyl-1,3-benzenediamine, N,N'-di-sec-butylidene-2,3-diethyl-1,4-benzenediamine, N,N'-di(2-butenylidene)-4,5,6-trihexyl-1,3-benzenediamine, N,N'-di(2,5-dimethylcyclopentylidene)-2,2'-methylenebis(benzeneamine), N,N'-dimenthylidene-2,3'-methylenebis(benzeneamine), N,N'-diisopropylidene-2,4'-methylenebis(benzeneamine), N,N'-di-sec-butylidene-3,3'-methylenebis(benzeneamine), N,N'-di(3-methyl-2-cyclohexenylidene)-3,4'-methylenebis(benzeneamine), N,N'-di(3,3-dimethyl-2-butylidene)-4,4'-methylenebis(benzeneamine), N,N'-di(3-pentylidene)-4,4'-(1,2-ethanediyl)bisbenzeneamine, N,N'-di(undecylidene)-3,4'-(1,3-propanediyl)bis(benzeneamine), N,N'-di(2,4-dimethyl-3-pentylidene)-2,2'-methylenebis(5-tert-butylbenzeneamine), N,N'-di(phorylidene)-3,3'-methylenebis(5-pentylbenzeneamine), N,N'-di(3-methylbutylidene)-3,3'-methylenebis(6-isopropylbenzeneamine), N,N'-di(2-heptylidene)-4,4'-methylenebis(2-methylbenzeneamine), N,N'-dimenthylidene-4,4'-methylenebis(3-sec-butylbenzeneamine), N,N'-di(1-cyclopentylethylidene)-4,4'-(1,2-ethanediyl)bis(2-methylbenzeneamine), and N,N'-di(1-penten-3-ylidene)-4,4'-methylenebis(2,3-di-sec-butylbenzeneamine).

B. Aromatic Secondary Diamines

Aromatic secondary diamines which are not compositions of the present invention that can be produced by the processes of the invention include, but are not limited to, N,N'-diisopropyl-1,2-benzenediamine, N,N'-di-sec-butyl-1,3-benzenediamine, N,N'-di(2-butenyl)-1,4-benzenediamine, N,N'-di-cyclopentyl-(4-ethyl-1,2-benzenediamine), N,N'-di-sec-butyl-(4-tert-butyl-1,3-benzenediamine), N,N'-di(1-cyclopropylethyl)-2-pentyl-1,4-benzenediamine, N,N'-di(4-hexyl)-(4-methyl-5-heptyl-1,3-benzenediamine), N,N'-dicyclopentyl-4,6-di-n-propyl-1,3-benzenediamine, N,N'-di-sec-butyl-(2,3-diethyl-1,4-benzenediamine), N,N'-di(1-penten-3-yl)-4,5,6-trihexyl-1,3-benzenediamine, N,N'-di(3-hexyl)-2,2'-methylenebis(benzeneamine), N,N'-di(2-cyclopentenyl)-2,3'-methylenebis(benzeneamine), N,N'-diisopropyl-2,4'-methylenebis(benzeneamine), N,N'-di-sec-butyl-3,3'-methylenebis(benzeneamine), N,N'-di(3-methyl-2-cyclohexenyl)-3,4'-methylenebis(benzeneamine), N,N'-di(3,3-dimethyl-2-butyl)-4,4'-methylenebis(benzeneamine), N,N'-di(10-undecenyl)-4,4'-(1,2-ethanediyl)bisbenzeneamine, N,N'-di(phoryl)-3,4'-(1,3-propanediyl)bis(benzeneamine), N,N'-di(2,4-dimethyl-3-pentyl)-2,2'-methylenebis(5-tert-butylbenzeneamine), N,N'-di(2,5-dimethylcyclopentyl)-3,3'-methylenebis(2-methylbenzeneamine), N,N'-di(isophoryl)-3,3'-methylenebis(5-pentylbenzeneamine), N,N'-di(2-hexyl)-3,3'-methylenebis(6-isopropylbenzeneamine), N,N'-dicyclohexyl-4,4'-methylenebis(3-sec-butylbenzeneamine), N,N'-di(1-cyclopentylethyl)-4,4'-(1,2-ethanediyl)bis(2-methylbenzeneamine), N,N'-diisopropyl-3, 3'-methylenebis(2,4-dipentylbenzeneamine), N,N'-di-sec-butyl-3,3'-methylenebis(5,6-diisopropylbenzeneamine), and N,N'-di(menthyl)-4,4'-methylenebis(2,3-di-sec-butylbenzeneamine).

C. Aliphatic Diimines

Aliphatic diimines that can be produced by the processes of the invention include, but are not limited to, N,N'-diisopropylidene-ethylenediamine, N,N'-di-sec-butylidene-1,2-diaminopropane, N,N'-di(2-butenylidene)-1,3-diaminopropane, N,N'-di(1-cyclopropylethylidene)-1,5-diaminopentane, N,N'-di(3,3-dimethyl-2-butylidene)-1,5-diamino-2-methylpentane, N,N'-di-sec-butylidene-1,6-diaminohexane, N,N'-di(3-pentylidene)-2,5-dimethyl-2,5-hexanediamine, N,N'-di(4-hexylidene)-1,2-diaminocyclohexane, N,N'-dicyclohexylidene-1,3-diaminocyclohexane, N,N'-di(1-cyclobutylethylidene)-1,4-diaminocyclohexane, N,N'-di(2,4-dimethyl-3-pentylidene)-1,3-cyclohexanebis(methylamine), N,N'-di(1-penten-3-ylidene)-1,4-cyclohexanebis(methyl amine), N,N'-diisopropylidene-1,7-diaminoheptane, N,N'-di-sec-butylidene-1,8-diaminooctane, N,N'-di(2-pentylidene)-1,10-diaminodecane, N,N'-di(3-hexylidene)-1,12-diaminododecane, N,N'-di(3-methyl-2-cyclohexenylidene)-1,2-diaminopropane, N,N'-di(2,5-dimethylcyclopentylidene)-1,4-diaminobutane, N,N'-di(isophorylidene)-1,5-diaminopentane, N,N'-di(menthylidene)-2,5-dimethyl-2,5-hexanediamine, N,N'-di(undecylidene)-1,2-diaminocyclohexane, N,N'-di-2-(4-methylpentylidene)-isophoronediamine, and N,N'-di(5-nonylidene)-isophoronediamine.

D. Aliphatic Secondary Diamines

Aliphatic secondary diamines that can be produced by the processes of the invention include, but are not limited to, N,N'-diisopropylethylenediamine, N,N'-di-sec-butyl-1,2-diaminopropane, N,N'-di(2-butenyl)-1,3-diaminopropane, N,N'-di(1-cyclopropylethyl)-1,5-diaminopentane, N,N'-di(3,3-dimethyl-2-butyl)-1,5-diamino-2-methylpentane, N,N'-di-sec-butyl-1,6-diaminohexane, N,N'-di(3-pentyl)-2,5-dimethyl-2,5-hexanediamine, N,N'-di(4-hexyl)-1,2-diaminocyclohexane, N,N'-dicyclohexyl-1,3-diaminocyclohexane, N,N'-di(1-cyclobutylethyl)-1,4-diaminocyclohexane, N,N'-di(2,4-dimethyl-3-pentyl)-1,3-cyclohexanebis(methylamine), N,N'-di(1-penten-3-yl)-1,4-cyclohexanebis(methylamine), N,N'-diisopropyl-1,7-diaminoheptane, N,N'-di-sec-butyl-1,8-diaminooctane, N,N'-di(2-pentyl)-1,10-diaminodecane, N,N'-di(3-hexyl)-1,12-diaminododecane, N,N'-di(3-methyl-2-cyclohexenyl)-1,2-diaminopropane, N,N'-di(2,5-dimethylcyclopentyl)-1,4-diaminobutane, N,N'-di(isophoryl)-1,5-diaminopentane, N,N'-di(menthyl)-2,5-dimethyl-2,5-hexanediamine, N,N'-di(undecyl)-1,2-diaminocyclohexane, N,N'-di-2-(4-methylpentyl)-isophoronediamine, and N,N'-di(5-nonyl)-isophoronediamine.

Formulations of the Invention

When the aromatic secondary diamines which are compositions of the invention are used as chain extenders in the preparation of polyurethane, polyurea, or polyurethane-urea polymers, they are used in place of the chain extenders that have previously been used in such processes, or they are used in conjunction with one or more known chain extenders, e.g., aromatic primary diamines such as those mentioned above; the aromatic polyamines of U.S. Pat. Nos. 3,428,610, 4,218,543, 4,595,742, and 4,631,298; polyhydroxyalkanes containing 2-6 carbons and 2-3 hydroxyl groups, such as ethylene glycol, the 1,2- and 1,3-propylene glycols, 1,4-, 1,2-, and 2,3-butanediols, 1,5-pentanediol, neopentyl glycol, 1,6-hexanediol, glycerol, 1,2,4-butanetriol, 1,2,6-hexanetriol; and mixtures of any two or more of the foregoing. Thus, the chain extender or mixture of chain extenders is reacted with an organic polyisocyanate and an active hydrogen-containing organic compound or with a prepolymer thereof having a free —NCO content of at least about 0.1% by weight to form the desired polymer. Whether the aromatic secondary diamines of the invention are used in place of or instead in conjunction with other chain extenders depends in part on the desired physical properties of the end product. Examples of isocyanates and active hydrogen-containing organic compounds that can be used are taught in, for example, U.S. Pat. No. 4,595,742.

When the aromatic secondary diamines which are compositions of this invention are to be used as curing agents for epoxy resins, they are used in place of the curing agents that have previously been used to cure such resins, or they are used in conjunction with one or more known curing agents, e.g., aromatic polyamines and/or polyhydroxyalkanes. Whether the aromatic secondary diamines of the invention are used in place of or instead in conjunction with other curing agents depends in part on the desired physical properties of the end product. The epoxy resin may be any epoxy resin, i.e., it may be saturated or unsaturated, aliphatic, cycloaliphatic, aromatic, or heterocyclic. Examples of such resins are taught in Lee et al., *Handbook of Epoxy Resins*, McGraw-Hill (New York), 1967.

Formulations of the invention are made from at least one polyol and/or at least one polyetheramine (sometimes referred to as an amine-terminated polyol), at least one isocyanate, and at least one aromatic secondary diamine which a composition of the invention; that is, an aromatic secondary diamine in which each amino hydrocarbyl group has at least two carbon atoms, wherein each position ortho to a secondary amino group bears a hydrocarbyl group, and which aromatic secondary diamine is either in the form of one benzene ring having two secondary amino groups on the ring, which secondary amino groups are meta or para relative to each other or is in the form of two benzene rings connected by an alkylene bridge and having one secondary amino group on each ring. As is well known in the art, other components may also be included in the formulations, such as one or more flame retardants, thermal stabilizers, and/or surfactants.

In the methods of the invention, a polyurethane, polyurea, or polyurea-urethane is made by blending together at least one polyol and/or at least one polyetheramine, at least one isocyanate, and at least one aromatic secondary diamine which a composition of the invention; that is, an aromatic secondary diamine in which each amino hydrocarbyl group has at least two carbon atoms, wherein each position ortho to a secondary amino group bears a hydrocarbyl group, and which aromatic secondary diamine is either in the form of one benzene ring having two secondary amino groups on the ring, which secondary amino groups are meta or para relative to each other or is in the form of two benzene rings connected by an alkylene bridge and having one secondary amino group on each ring. Usually, the polyol or polyetheramine, aromatic secondary diamine, and when used, optional ingredients, are blended together to form a first mixture, followed by blending this first mixture with the isocyanate to form a second mixture. This second mixture is allowed to cure.

The following examples are presented for purposes of illustration, and are not intended to impose limitations on the scope of this invention.

In the Examples below, the Pt(S)/C (Engelhard Corporation) is in powdered form, unless otherwise specified.

EXAMPLE 1

4,4'-Methylenebis(2,6-diethylbenzeneamine) (4.0 g), Pt(S)/C (0.2 g), sulfonated divinylbenzene/styrene copolymer (0.2 g; H ion form, sold as Amberlyst-15 by Rohm and Haas Company, Philadelphia, Pa.), and methyl ethyl ketone (50 g) were charged into a 100 mL metal autoclave at 22° C. The closed autoclave was purged 3 times with 125 psig ($9.63 \times 10^5$ Pa) of $H_2$ at 22° C. to remove traces of air. The reaction mixture was then heated at 95° C. under 125 psig ($9.63 \times 10^5$ Pa) of $H_2$ for 3 hours (until no further $H_2$ uptake was observed). The product mixture was cooled to 22° C. and degassed. A diluted product sample was analyzed by gas chromatography (GC; 180° C. for 5 minutes at 10° C. per minute rate; final temperature, 270° C.). The GC data (normalization method) showed 100% conversion of 4,4'-methylenebis(2,6-diethylbenzeneamine) and a 94% yield of N,N'-di-sec-butyl-4,4'-methylenebis(2,6-diethylbenzeneamine). NMR analysis (with internal standard) of a neat product sample showed a purity of 94.75%.

EXAMPLE 2

Diethyl(methyl)-1,3-benzenediamine, as a mixture of its 2,4-diethyl-6-methyl- and 4,6-diethyl-2-methyl-isomers (10.0 g; Ethacure® 100, Albemarle Corporation), Pt(S)/C (0.5 g), Amberlyst-15 (0.5 g), and methyl ethyl ketone (50 g) were charged into a 100 mL metal autoclave at 22° C. The closed autoclave was purged 3 times with 125 psig ($9.63 \times 10^5$ Pa) of $H_2$ at 22° C. to remove traces of air. The reaction mixture was then heated at 120° C. under 125 psig ($9.63 \times 10^5$ Pa) of $H_2$ for 5.5 hrs (until no further $H_2$ uptake was observed). The product mixture was cooled to 22° C. and degassed. A diluted product sample was analyzed by GC (100° C. for 5 minutes at 10° C. per minute rate; final temperature, 270° C.). The GC data (normalization method) showed 100% conversion of diethyl(methyl)-1,3-benzenediamine, and a 96.5% yield of N,N'-di-sec-butyl-[diethyl(methyl)-1,3-benzenediamine].

EXAMPLE 3

4,4'-Methylenebis(2,6-diethylbenzeneamine) (3 g), Pt(S)/C (0.3 g), Amberlyst-15 (0.3 g), methyl ethyl ketone (25 g), and tetrahydrofuran (THF; 25 g) were charged into a 100 mL metal autoclave at 22° C. The closed autoclave was purged 3 times with 90 psig ($7.22 \times 10^5$ Pa) of $H_2$ at 22° C. The reaction mixture was then heated at 100-120° C. under 125 psig ($9.63 \times 10^5$ Pa) of $H_2$ for 5 hrs (until no further $H_2$ uptake was observed). The product mixture was cooled to 22° C. and degassed. A diluted product sample was analyzed by GC (180° C. for 5 minutes at 10° C. per minute rate; final temperature, 270° C.). The GC data (normalization method) showed 100% conversion of 4,4'-methylenebis(2,6-diethylbenzeneamine), and an 86% yield of N,N'-di-sec-butyl-4,4'-methylenebis(2,6-diethylbenzeneamine).

EXAMPLE 4

Diethyl(methyl)-1,3-cyclohexanediamine, as a mixture of its 2,4-diethyl-6-methyl- and 4,6-diethyl-2-methyl-isomers was made by hydrogenating diethyl(methyl)-1,3-benzenediamine, as a mixture of its 2,4-diethyl-6-methyl- and 4,6-diethyl-2-methyl-isomers (Ethacure® 100) according to known procedures; see for example U.S. Pat. No. 4,161,492.

Diethyl(methyl)-1,3-cyclohexanediamine, as a mixture of its 2,4-diethyl-6-methyl- and 4,6-diethyl-2-methyl-isomers (3.0 g), Pt(S)/C (0.4 g), Amberlyst-15 (0.4 g), and methyl ethyl ketone (45 g) were charged into a 100 mL metal autoclave at 22° C. The closed autoclave was purged 3 times with 125 psig ($9.63 \times 10^5$ Pa) of $H_2$ at 22° C. to remove traces of air. The reaction mixture was then heated at 130° C. under 125 psig ($9.63 \times 10^5$ Pa) of $H_2$ for 6 hrs (until no further $H_2$ uptake was observed). The product mixture was cooled to 22° C. and degassed. A diluted product sample was analyzed by GC (100° C. for 5 minutes at 10° C. per minute rate; final temperature, 270° C.). The GC data (normalization method) showed 100% conversion of diethyl(methyl)-1,3-cyclohexanediamine, and a 95-97% yield of N,N'-di-sec-butyl-[diethyl(methyl)-1,3-cyclohexanediamine].

EXAMPLE 5

Diethyl(methyl)-1,3-cyclohexanediamine, as a mixture of its 2,4-diethyl-6-methyl- and 4,6-diethyl-2-methyl-isomers was made as described in Example 4. Diethyl(methyl)-1,3-cyclohexanediamine, as a mixture of its 2,4-diethyl-6-methyl- and 4,6-diethyl-2-methyl-isomers (10 g), Pt(S)/C (0.5 g), Amberlyst-15 (0.5 g), and acetone (50 g) were charged into a 100 mL metal autoclave at 22° C. The closed autoclave was purged 3 times with 125 psig ($9.63 \times 10^5$ Pa) of $H_2$ at 22° C. to remove traces of air. The reaction mixture was then heated at 110-130° C. under 125 psig ($9.63 \times 10^5$ Pa) of $H_2$ for 8 hrs (until no further $H_2$ uptake was observed). The product mixture was cooled to 22° C. and degassed. A diluted product sample was analyzed by GC (100° C. for 5 minutes at 10° C. per minute rate; final temperature, 270° C.). The GC data (normalization method) showed 100% conversion of diethyl(methyl)-1,3-cyclohexanediamine, and a 95-97% yield of N,N'-diisopropyl-[diethyl(methyl)-1,3-cyclohexanediamine].

EXAMPLE 6

A two-liter three neck round bottom flask was equipped with a heating mantle, a thermocouple, a glass stopper and a condenser. 4,4'-Methylenebis(2,6-diethylbenzeneamine) (200 g, 0.644 mol) and acetone (200 mL, 158 g, 2.72 mol) were added to the flask. After the 4,4'-methylenebis(2,6-diethylbenzeneamine) had dissolved in the acetone, molecular sieves (200 g) and Amberlyst-15 (20 g) were added to the flask. Molecular sieves were used to remove water as it formed in the reaction. The mixture was heated to reflux. Samples were periodically taken and analyzed by GC. After 24 hours, 18% of the starting diamine remained. The reaction mixture was filtered, and returned to the reaction flask. Fresh molecular sieves (200 g) and fresh Amberlyst-15 (20 g) were added to the filtered mixture in the reaction flask. More acetone (170 mL) was also added to the reaction mixture. GC analysis of this mixture showed 94.4 area % N,N'-diisopropylidene-4,4'-methylenebis(2,6-diethylbenzeneamine), 3.7 area % N-isopropylidene-4,4'-methylenebis(2,6-diethylbenzeneamine), and 0.2 area % 4,4'-methylenebis(2,6-diethylbenzeneamine).

N,N'-diisopropylidene-4,4'-methylenebis(2,6-diethylbenzeneamine) (2.6 g) and Pt(S)/C (0.35 g) were added to a mixture of ethanol (20 g) and ethyl acetate (20 g) in an autoclave. The closed autoclave was purged 3 times with 125 psig ($9.63 \times 10^5$ Pa) of $H_2$ at 22° C. to remove traces of air. The mixture was kept at 22° C. and 0-125 psi (0 to $8.62 \times 10^5$ Pa) of $H_2$ for 1.2 hours, forming the corresponding N,N'-diisopropyl-4,4'-methylenebis(2,6-diethylbenzeneamine) in 70% yield, with 25% of the diimine underhydrogenated. Conversion of the diimine was 95%.

EXAMPLE 7

Diethyl(methyl)-1,3-benzenediamine (Ethacure® 100; 30 g, 0.17 mol), acetone (150 mL, 117 g, 2.0 mol), Amberlyst-15 (2 g), and molecular sieves (64.1 g) were added to a one-pint bottle. Occasionally, the bottle was rolled and the mixture was analyzed by GC. After 19 days, GC analysis showed 88.5 area % of N,N'-diisopropylidene-[diethyl(methyl)-1,3-benzenediamine] (includes both isomers) and 10.1 area % of N-isopropylidene-[diethyl(methyl)-1,3-benzenediamine] (includes three isomers).

N,N'-diisopropylidene-[diethyl(methyl)-1,3-benzenediamine] (3.17 g) and Pt(S)/C (0.3 g) were added to a mixture of ethanol (20 g) and ethyl acetate (20 g) in an autoclave. The closed autoclave was purged 3 times with 125 psig (9.63×10$^5$ Pa) of H$_2$ at 22° C. to remove traces of air. The mixture was kept at 22° C. and 0-125 psi (0 to 8.62×10$^5$ Pa) of H$_2$ for 1.2 hours, forming the corresponding N,N'-diisopropyl-[diethyl(methyl)-1,3-benzenediamine] in 94% yield. Six percent of the diimine was underhydrogenated; conversion of the diimine was 100%.

EXAMPLE 8

A two-liter three neck round bottom flask was equipped with a magnetic stirrer, a heating mantle, a thermocouple, a glass stopper and a Dean Stark trap fitted with a condenser. 4,4'-Methylenebis(2,6-diethylbenzeneamine) (310.5 g, 1.00 mol) and methyl ethyl ketone (450 mL, 350 g, 4.85 mol) were added to the flask. This mixture was stirred at 40° C. to dissolve the 4,4'-methylenebis(2,6-diethylbenzeneamine). Hexanes (300 mL) and Amberlyst-15 (15.54 g) were added to the flask. The mixture was heated to reflux, and water was removed as an azeotrope in the Dean Stark trap. Samples were periodically taken and analyzed by gas chromatography (GC). N,N'-di-sec-butylidene-4,4'-methylenebis(2,6-diethylbenzeneamine) was formed in 94.7% yield. GC results are summarized in Table 1; units for the diamine, monoimine, and diimine are GC area percent.

N,N'-di-sec-butylidene-4,4'-methylenebis(2,6-diethylbenzeneamine) (22.53 g) and Pt(S)/C (2.65 g) were added to acetone (34.0 g) in an autoclave. The closed autoclave was purged 3 times with 125 psig of H$_2$ (9.63×10$^5$ Pa) at 22° C. The mixture was kept at 21° C. and 125 psi (8.62×10$^5$ Pa) of H$_2$ for 6.5 hours, forming the corresponding N,N'-di-sec-butyl-4,4'-methylenebis(2,6-diethylbenzeneamine) quantitatively.

TABLE 1

| Time at reflux | Water collected | Diamine | Monoimine | Diimine |
|---|---|---|---|---|
| 0 hr | 0 g | 95.8 | 4.0 | 0 |
| 3 hr | 9.0 g | 64.6 | 31.6 | 3.6 |
| 19 hr | 33.0 g | 4.5 | 33.1 | 62.1 |
| 22 hr | 36.0 g | 2.0 | 24.9 | 72.9 |
| 26 hr | 39.6 g | 1.1 | 16.8 | 81.8 |
| 26 hr | 39.7 g | 0.7 | 14.8 | 84.3 |
| 29 hr | 41.1 g | 0.3 | 9.6 | 89.9 |
| 49 hr | 42.3 g | 0.5 | 4.4 | 94.7 |

EXAMPLE 9

A two-liter three neck round bottom flask was equipped with a magnetic stirrer, a heating mantle, a thermocouple attached to a thermowatch, and a condenser fitted with a nitrogen inlet. 3,5-Diethyl(methyl)-1,3-benzenediamine (Ethacure® 100; 100 g, 0.562 mol) and methyl ethyl ketone (200 g, 2.77 mol) were added to the flask. Amberlyst-15 (20 g) and molecular sieves (200 g) were added to the flask. The mixture was heated to reflux; the pot temperature was 85° C. Samples were periodically taken and analyzed by GC. Table 2 summarizes the GC area % conversion over time. After 6 hours, an additional 50 g of molecular sieves were added. The reaction product mixture was filtered through a sintered glass funnel to remove Amberlyst-15 and the molecular sieves. Methyl ethyl ketone was removed via distillation to give 138 g of N,N'-di-sec-butylidene-[diethyl(methyl)-1,3-benzenediamine].

N,N'-di-sec-butylidene-[diethyl(methyl)-1,3-benzenediamine] (28 g) and Pt(S)/C (2.8 g) were added to acetone (30 g) in an autoclave. The closed autoclave was purged 3 times with 125 psig (9.63×10$^5$ Pa) of H$_2$ at 22° C. The mixture was kept at 21° C. and 125 psi (8.62×10$^5$ Pa) of H$_2$ for 12 hours, forming the corresponding N,N'-di-sec-butyl-[diethyl(methyl)-1,3-benzenediamine] quantitatively.

TABLE 2

| | Diamine | | Monoimine | | | Diimine | |
|---|---|---|---|---|---|---|---|
| | | | Isomer: | | | | |
| Time at reflux | 2,4- | 2,6- | 2,4- | 2,4- | 2,6- | 2,4- | 2,6- |
| 0.25 hr | 48.8 | 6.4 | 10.3 | 14.7 | 12.3 | 2.4 | 2.3 |
| 3 hr | 3.6 | 0.2 | 14.1 | 27.7 | 4.9 | 31.1 | 15.9 |
| 6 hr | 0.3 | — | 6.0 | 15.4 | 1.4 | 56.2 | 18.9 |
| 7 hr | 0.3 | — | 4.5 | 11.5 | 1.2 | 62.0 | 18.8 |
| 12 hr | 0.2 | — | 3.9 | 6.8 | 1.5 | 67.5 | 18.1 |
| 28 hr | — | — | 2.7 | 2.6 | 1.1 | 72.7 | 18.2 |
| Final product | — | — | 2.4 | 2.3 | 0.9 | 72.9 | 18.2 |

EXAMPLE 10

The first run (Run 1) was performed in a 2 liter Parr reactor, and Runs 2-5 were done in a 10 gallon stainless steel reactor (Autoclave Engineers, Erie, Pa.). Diethyl(methyl)-1,3-benzenediamine, as a mixture of its 2,4-diethyl-6-methyl- and 4,6-diethyl-2-methyl-isomers (Ethacure® 100, Albemarle Corporation) was charged to the reactor, followed by methyl ethyl ketone (MEK), then Pt(S)/C, and then Amberlyst-15. Amounts of reagents used in each run are listed in Table 3. The reactor was sealed and purged three times with H$_2$ and then the reactor was pressured with H$_2$ to about 75 to 130 psig (6.18×10$^5$ to 9.98×10$^5$ Pa). The reactor contents were stirred at 115 to 130° C. for 9 to 24 hours at 75 to 135 psig (6.18×10$^5$ to 1.03×10$^6$ Pa). Specific pressure and temperature ranges for each run are listed in Table 3. The reaction mass in the reactor was cooled, and the reactor was vented and purged with nitrogen 3 times. The reaction masses from the 10 gallon reactor were pressured though a pair of 10-inch (25.4 cm) 0.5-micron cartridge filters in parallel to remove the Pt(S)/C and Amberlyst-15. Due to the higher concentration in the reaction masses from Runs 2 and 3, additional MEK was added before pressuring the reaction mass through the cartridge filters to reduce the time required for the filtration (removal of the catalysts). Results are summarized in Table 3. Conversion, yield, and partially reacted amounts reported in Table 3 were determined by GC (100° C. for 5 minutes at 10° C. per minute rate; final temperature, 270° C.).

The reaction masses from Runs 2, 3, 4, and 5, and 1000 g of the final reaction mass from Run 1 were combined into a 100 liter reactor as space permitted. Each reaction mass was filtered with a 10-inch, 0.5-micron cartridge filter into the 100 liter reactor. The bulk of the MEK was removed at atmospheric pressure. The combined product was distilled at less than 1 torr (133 Pa) at 134 to 141° C. to give 2.189 g of a forecut, 30.0 kg of a main cut, and 2370 g of dark distillation pot bottoms. By GC area %, it appeared that most of the distillation pot bottoms were the product, N,N'-di-sec-butyl-[diethyl(methyl)-1,3-benzenediamine]. The distillation pot bottoms were flashed twice using a wiped film evaporator to give an additional 2.254 kg of product which was added to the 30.0 kg main cut. The forecut was sent back through the wiped film evaporator twice; the first pass was to remove the lower boiling impurities and the second pass was to obtain additional product (1408 g). This additional product was combined with the 30 kg and 2.254 kg product to give 33.6 kg of the final product as a yellow liquid (94% yield, not corrected for purity). The composition of this material was 78.85 area % N,N'-di-sec-butyl-[2,4-diethyl-6-methyl-1,3-benzenediamine] and 16.67 area % N,N'-di-sec-butyl-[4,6-diethyl-2-methyl-1,3-benzenediamine].

per minute rate; final temperature, 270° C.). The GC data (normalization method) showed 100% conversion of diethyl (methyl)-1,3-benzenediamine, and an 88.8% yield of N,N'-di-sec-butyl-[diethyl(methyl)-1,3-benzenediamine].

EXAMPLE 13

4,4'-Methylenebis(benzeneamine) (1.98 g, 10 mmol), acetone (10.0 g, 172 mmol), Pt(S)/C (0.2 g), and toluene (50.0 g) were charged into reactor. The reactor was purged 3 times with 110 psig ($8.60 \times 10^5$ Pa) of $H_2$ at 22° C. The reaction mixture was then stirred at 60° C. under 110 psig of $H_2$ for 2 hours. GC (conditions: 180° C./5 minutes/10° C.-minutes rate/270° C./RT=9.37 minutes) showed 100% conversion of 4,4'-methylenebis(benzeneamine), and a 97% yield of N,N'-diisopropyl-4,4'-methylenebis(benzeneamine). The structure

TABLE 3

| Compound | Run 1 | Run 2 | Run 3 | Run 4 | Run 5 |
| --- | --- | --- | --- | --- | --- |
| Ethacure ® 100 | 252 g | 4756 g | 5064 g | 3980 g | 4020 g |
| MEK | 1.0 kg | 14.01 kg | 15.09 kg | 16.57 kg | 16.5 kg |
| Pt(S)/C | 12.5 g | 254 g | 256 g | 200 g | 204 g |
| Amberlyst-15 | 12.5 g | 250 g | 250 g | 200 g | 200 g |
| MEK added after reaction | | 5.0 kg | 5.0 kg | none | none |
| MEK rinse | | 5.0 kg | 4.9 kg | 4.96 kg | 9367 kg |
| $H_2$ Pressure | 76-125 psig ($6.25 \times 10^5$-$9.63 \times 10^5$ Pa) | 120-127 psig ($9.29 \times 10^5$-$9.77 \times 10^5$ Pa) | 120-132 psig ($9.29 \times 10^5$-$1.01 \times 10^6$ Pa) | 119-120 psig ($9.22 \times 10^5$-$9.29 \times 10^5$ Pa) | 120-193 psig ($9.29 \times 10^5$-$1.43 \times 10^6$ Pa) |
| Temperature | 121-132° C. | 126-133° C. | 118-130° C. | 115-117° C. | 125-127° C. |
| Stirring time | 24 hrs | 22 hrs | 19 hrs | 19 hrs | 9 hrs |
| Conversion | 100% | 100% | 100% | 100% | 100% |
| Yield | 96.5% | 94% | 96.0% | 95.9% | 95.5% |
| Partially reacted* | 3.5% | 3.3% | 1.7% | 1.8% | 1.7% |

*The partially reacted species found in the GC were identified as diimines (unhydrogenated) or a compound with a secondary amino group and an imino group (partially hydrogenated).

EXAMPLE 11

Isophorone diamine (10 g), 5-nonanone (20 g), Amberlyst-15 (0.3 g), and Pt(S)/C (0.7 g) were charged into a 100 mL metal autoclave at 22° C. The autoclave was purged 3 times with 111 psig ($8.67 \times 10^5$ Pa) of $H_2$ at 22° C. The reaction mixture was then heated to and stirred at 116-121° C. under 111 psig of $H_2$ for 10 hours. GC indicated incomplete hydrogenation, so additional Amberlyst-15 (0.3 g) and Pt(S)/C (0.5 g) were added to the autoclave. The reaction mixture was stirred at 110-130° C. under 93 psig ($7.43 \times 10^5$ Pa) of $H_2$ for 24 hours. GC indicated 100% conversion of the starting materials, and a 93.6% yield of the product, N,N'-di-(5-nonyl)-isophoronediamine.

EXAMPLE 12

Diethyl(methyl)-1,3-benzenediamine, as a mixture of its 2,4-diethyl-6-methyl- and 4,6-diethyl-2-methyl-isomers (5 g; Ethacure® 100, Albemarle Corporation), Pt(S)/C (0.5 g), water (1 g) and methyl ethyl ketone (50 g) were charged into a 100 mL metal autoclave at 22° C. The autoclave was purged 3 times with 125 psig ($9.63 \times 10^5$ Pa) of $H_2$ at 22° C. The reaction mixture was then heated at 130° C. under 125 psig ($9.63 \times 10^5$ Pa) of $H_2$. After 30-45 minutes, $H_2$ uptake was observed. The reaction mixture was stirred at 130° C. for 8 hours (until no further $H_2$ uptake was observed). The product mixture was cooled to 22° C. and degassed. A diluted product sample was analyzed by GC (100° C. for 5 minutes at 10° C.

of the product was confirmed by GC-MS. No tertiary diamine was detected either by GC or by GC-MS.

EXAMPLE 14

4,4'-Methylenebis(benzeneamine) (8.0 g, 40 mmol), acetone (10.0 g, 172 mmol), Pt(S)/C (0.5 g), and toluene (50.0 g) were charged into reactor. The reactor was purged 3 times with 110 psig ($8.60 \times 10^5$ Pa) of $H_2$ at 22° C. The reaction mixture was then stirred at 22° C. under 110 psig of $H_2$ overnight. GC (conditions: 180° C./5 minutes/10° C.-minutes rate/270° C./RT=9.37 minutes) showed 100% conversion of 4,4'-methylenebis(benzeneamine), and a 98% yield of N,N'-diisopropyl-4,4'-methylenebis(benzeneamine). The structure of the product was confirmed by GC-MS. No tertiary diamine was detected either by GC or by GC-MS.

EXAMPLE 15

4,4'-Methylenebis(2,6-dimethylbenzeneamine) (1.25 g), methyl ethyl ketone (15 g), Pt(S)/C (0.10 g), and toluene (40.0 g) were charged into reactor. The reactor was purged 3 times with 110 psig ($8.60 \times 10^5$ Pa) of $H_2$ at 22° C. The reaction mixture was then stirred at 22° C. under 110 psig of $H_2$ for 4.5 hours. GC (conditions: 100° C./5 minutes/10° C.-minute/ 270° C.) showed 35% conversion of 4,4'-methylenebis(2,6-dimethylbenzeneamine). The reaction mixture was then stirred for 4 hours at 60° C., after which GC showed 79.5% conversion of 4,4'-methylenebis(2,6-dimethylbenzeneamine). The reaction mixture was then stirred for 11 hours at 130° C., after which GC showed 100% conversion of 4,4'-methylenebis(2,6-dimethylbenzeneamine), and a 96% yield of N,N'-di-sec-butyl-4,4'-methylenebis(2,6-dimethylbenzeneamine); the remaining 4% was determined to be N-sec-butyl-4,4'-methylenebis(2,6-dimethylbenzeneamine). The product was observed to be water-white in color, and the structure of the product was confirmed by GC-MS.

EXAMPLE 16

4,4'-Methylenebis(benzeneamine) (MDA; 1.20 g), Pt(S)/C (1.20 g), and 2-butanone (methyl ethyl ketone, MEK; 50.0 g) were charged to an autoclave. The autoclave was degassed three times with $H_2$ at 22° C. and the mixture was heated to 120° C. under 14 psig ($1.98 \times 10^5$ Pa) $H_2$ without stirring. At 120° C., with stirring, the autoclave was pressurized to 85 psig ($6.87 \times 10^5$ Pa) with $H_2$ over a period of twelve minutes. The reaction mixture was then cooled to 22° C. GC analysis showed 100% conversion of MDA, and a 96% yield of N,N'-di(2-butyl)-4,4'-methylenebis(benzeneamine).

EXAMPLE 17

Isophorone diamine (12.0 g), 4-methyl-2-pentanone (methyl isobutyl ketone, 50.0 g), Pt(S)/C (0.5 g, 4.25 wt % relative to isophorone diamine), and toluene were charged into a 100 mL autoclave, which was purged 3 times with 110 psig ($8.60 \times 10^5$ Pa) of H2 at 22° C. The reaction mixture was stirred at 120° C. under 110 psig of $H_2$ for 8 hours. GC indicated 100% conversion of isophorone diamine, and a 95% yield of N,N'-di-(4-methyl-2-pentyl)-isophorone diamine. The gel time of N,N'-di-(4-methyl-2-pentyl)-isophoronediamine in a polyurea formulation similar to those in Examples 29-32 (see below) was 22 seconds.

EXAMPLE 18

Isophorone diamine (9.0 g), 4-methyl-2-pentanone (50.0 g), and Pt(S)/C (0.09 g, 1 wt % relative to isophorone diamine), were charged into a 100 mL autoclave, which was purged 3 times with 111 psig ($8.67 \times 10^5$ Pa) of 112 at 22° C. The reaction mixture was then heated to 135° C. and stirred at 135° C. under 111 psig of $H_2$ for 7 hours. GC indicated 100% conversion of isophorone diamine, and a 98% yield of N,N'-di-(4-methyl-2-pentyl)-isophorone diamine. GC (conditions: 70°/5 minutes/10° C.-minutes rate/270° C./RT=16.3-16.9 minutes/5 isomers) indicated a 100% conversion of the starting materials, and a yield of at least 98% of N,N'-di-(4-methyl-2-pentyl)-isophoronediamine.

EXAMPLE 19

Isophorone diamine, 4-methyl-2-pentanone, and Pt(S)/C (10 wt % relative to isophorone diamine), were charged into a 100 mL autoclave, which was purged 3 times with 111 psig ($8.67 \times 10^5$ Pa) of $H_2$ at 22° C. The reaction mixture was then heated to 136° C. and stirred at 135° C. under 111 psig of $H_2$ for 1 hour. GC indicated a 100% conversion of starting materials, and nearly quantitative yield of N,N'-di-(4-methyl-2-pentyl)-isophoronediamine.

EXAMPLE 20

Isophoronediamine (1.0 g), Pt(S)/C (1.0 g), and 4-methyl-2-pentanone (methyl isobutyl ketone, MIBK; 50 g) were charged to a 100 mL autoclave. The autoclave was degassed with $H_2$ (14 psig; $1.98 \times 10^5$ Pa) at 22° C. and mixture heated to 135° C. for about 30 minutes. When the mixture reached 135° C., the autoclave was pressurized to 111 psig ($8.67 \times 10^5$ Pa) with $H_2$. The reaction mixture was kept at 135-140° C. under 111 psig $H_2$ for 3.5 minutes. The reaction was stopped by quenching with ice water. GC analysis (70° C./5 minutes/ 10° C. per minute heating rate) showed 100% conversion of isophoronediamine, a trace of primary amine, traces of ketimine intermediates, and a 96% yield of N,N'-di-[2-(4-methylpentyl)]-isophoronediamine. No tertiary amine was observed by GC.

EXAMPLE 21

The procedure of Example 20 was repeated, except that 5.0 g isophoronediamine, 5.0 g Pt(S)/C, and 50 g MIBK were used, and the reaction time after reaching 135° C. was 24 minutes. GC analysis showed 100% conversion of isophoronediamine, some primary amine, some ketimine, 95% yield of N,N'-di-[2-(4-methylpentyl)]-isophoronediamine, and no tertiary amine.

EXAMPLE 22

Isophoronediamine (5 g), Pt(S)/C (5 g), and 4-methyl-2-pentanone (MIBK; 54 g) were charged to a 100 mL autoclave. The autoclave was degassed three times with $H_2$ (111 psig; $8.67 \times 10^5$ Pa) at 22° C. and mixture heated to 135° C. for about 30 minutes. The reaction mixture was cooled to 22° C. and degassed. The reaction was stopped by quenching with ice water. GC analysis showed 100% conversion of isophoronediamine, and a 98% yield of N,N'-di-[2-(4-methylpentyl)]-isophoronediamine.

EXAMPLE 23

The procedure of Example 22 was repeated, except that 10 g isophoronediamine, 5 g Pt(S)/C, and 54 g MIBK were used. GC analysis showed 4% isophoronediamine, 2.3% ketimine, 93.7% N,N'-di-[2-(4-methylpentyl)]-isophoronediamine; no tertiary amines were observed.

EXAMPLE 24

Isophorone diamine (10.0 g, 58.7 mmol), 5-nonanone (20.0 g, 140.5 mmol), toluene (35 g), Amberlyst-15 (6 wt % relative to isophorone diamine), and Pt(S)/C (12 wt % relative to isophorone diamine) were charged into a reactor. The reactor was purged 3 times with $H_2$. The reaction mixture was then heated to and stirred at 116-130° C. under 111-113 psig ($8.67 \times 10^5$ to $8.82 \times 10^5$ Pa) of $H_2$ for 39 hours. GC indicated a 100% conversion of isophorone diamine and a 97 area % yield of desired product, which was then identified and confirmed by GC-MS. The gel time of N,N'-di-5-nonyl-isophoronediamine in a polyurea formulation similar to those in Examples 29-32 (see below) was 59 seconds.

EXAMPLE 25

Isophorone diamine (17 g, 100 mmol), 4-heptanone (34.2 g, 300 mmol), Pt(S)/C (0.85 g), and toluene (20 g) were charged to a 100 mL autoclave. The autoclave was degassed three times with $H_2$ and then the mixture was heated to 120-130° C. for about 30 hours under 112 psig ($8.74 \times 10^5$ Pa) of H$_2$. The reaction mixture was cooled to 22° C. and degassed. GC analysis showed a 96% yield of N,N'-di(4-heptyl)-isophoronediamine. The structure of the product was confirmed by GC-MS. The gel time of N,N'-di-(4-heptyl)-isophoronediamine in a polyurea formulation similar to those in Examples 29-32 (see below) was 55 seconds.

EXAMPLE 26

4,4'-Methylenebis(benzeneamine) (MDA; 2.0 g), granular Pt(S)/C (1.0 g, Johnson Matthey), and methyl ethyl ketone (50.0 g) were charged to a 100 mL autoclave. The autoclave was degassed three times with H$_2$ and then the mixture was heated at 121° C. for 2 hours under 85 psig (6.87×10$^5$ Pa) of H$_2$. The reaction mixture was cooled to 22° C. and degassed. The granular Pt(S)/C catalyst settled to the bottom of reactor as soon as the agitation was stopped, making it easier to decant the product solution and recover the catalyst. GC analysis showed a 95% yield of N,N'-di(2-butyl)-4,4'-methylenebis(benzeneamine), and less than 0.4 area % of overalkylated side-product.

EXAMPLE 27

4,4'-Methylenebis(benzeneamine) (19.8 g, 0.1 mol), methyl ethyl ketone (20.0 g, 0.28 mol), Pt(S)/C (2.0 g), and water (28.0 g; formed a second phase) were charged into reactor. The reactor was purged 3 times with H$_2$ at 22° C. The reaction mixture was then stirred at 800 rpm at 136° C. under H$_2$ for 2.5 hours. GC showed 100% conversion of 4,4'-methylenebis(benzeneamine), and a 96-97% yield of N,N'-di-sec-butyl-4,4'-methylenebis(benzeneamine).

EXAMPLE 28

A heated stainless steel tubular upflow reactor is used. The reactor is packed with Pt(S)/C. Isophoronediamine and 4-methyl-2-pentanone are co-fed to the reactor. The isophoronediamine is fed at a rate of 0.5 g per minute, and 4-methyl-2-pentanone is fed at a rate of 5 g per minute. Hydrogen is also co-fed into the reactor with the isophoronediamine and the 4-methyl-2-pentanone. Conditions in the reactor are 100 psig and 140° C. The yield of N,N'-di-[2-(4-methylpentyl)]-isophoronediamine is 96%; no tertiary amines are observed.

EXAMPLE 29

Polyurethane formulations containing isocyanate (15.2% NCO, Rubinate® 9480, Huntsman Chemical), a polyol (a triol with molecular weight 5000, Voranol® 4703, Dow Chemical Company), a mixture of 2,4-diethyl-6-methyl-1,3-benzenediamine and 4,6-diethyl-2-methyl-1,3-benzenediamine (Ethacure® 100, Albemarle Corporation), N,N'-di-sec-butyl-[diethyl(methyl)-1,3-benzenediamine], and dibutyl tin dilaurate (DABCO® T-12, Air Products and Chemicals, Inc., Allentown, Pa.) were prepared; one formulation was prepared without N,N'-di-sec-butyl-[diethyl(methyl)-1,3-benzenediamine], for comparative purposes. All ingredients except the isocyanate were mixed together in a blender for five minutes and then degassed in an oven; amounts of the components in this mixture are listed in Table 4. The mixture was placed in one barrel of a two-barrel syringe; the isocyanate was placed in the other barrel. The syringe contents were blended by pushing them through a static mixer onto a steel plate and cured at room temperature. A 1:1 volume ratio of isocyanate to the mixture resulted from the blending of the syringe contents. The cured formulations were then subjected to testing. Properties of the formulations are summarized in Table 4.

TABLE 4

| Component | Formulation 1 | Formulation 2 | Formulation 3 | Formulation 4 |
| --- | --- | --- | --- | --- |
| Polyol | 69.3 wt % | 63.0 wt % | 60.5 wt % | 56.6 wt % |
| Ethacure ® 100 | 30.5 wt % | 24.5 wt % | 19.5 wt % | 16.5 wt % |
| N,N'-di-sec-butyl-[diethyl(methyl)-1,3-benzenediamine] | 0 | 12.4 wt % | 20.0 wt % | 26.8 wt % |
| dibutyl tin dilaurate | 0.1 wt % | 0.1 wt % | 0.1 wt % | 0.1 wt % |
| Static mixer units | 48 | 48 | 48 | 48 |
| Gel time (cure rate) | 3 | 4 | 4 | |
| Shore D hardness, 0 sec. | 49 | 46 | 42 | 35 |
| Shore D hardness, 10 sec. | 43 | 41 | 36 | 30 |
| Tensile strength | 2940 psi (2.03 × 10$^7$ Pa) | 2840 psi (1.96 × 10$^7$ Pa) | 1850 psi (1.28 × 10$^7$ Pa) | 1430 psi (9.9 × 10$^6$ Pa) |
| Elongation | 360% | 400% | 350% | 360% |
| Modulus (100%) | 1470 psi (1.0 × 10$^7$ Pa) | 1250 psi (8.6 × 10$^6$ Pa) | 960 psi (6.6 × 10$^6$ Pa) | 760 psi (5.2 × 10$^6$ Pa) |
| Modulus (300%) | 2540 psi (1.8 × 10$^7$ Pa) | 2250 psi (1.6 × 10$^7$ Pa) | 1640 psi (1.1 × 10$^7$ Pa) | 1280 psi (8.8 × 10$^6$ Pa) |
| Tear strength | 440 pli | 350 pli | 290 pli | 230 pli |

EXAMPLE 30

Polyurea formulations containing isocyanate (14.9% NCO, Rubinate® 9480, Huntsman Chemical), Jeffamine® D-2000 and Jeffamine® T-5000 (amine-terminated polyols or polyetheramines, Huntsman Chemical), Ethacure® 100, and N,N'-di-sec-butyl-[diethyl(methyl)-1,3-benzenediamine] were prepared as described in Example 29; one formulation was prepared without N,N'-di-sec-butyl-[diethyl (methyl)-1,3-benzenediamine], for comparative purposes. Amounts of the components of the mixture that was blended with the isocyanate in each formulation are listed in Table 5. The cured formulations were subjected to testing. Properties of the formulations are summarized in Table 5.

TABLE 5

| Component | Formulation 1 | Formulation 2 | Formulation 3 |
|---|---|---|---|
| Amine-terminated polyol (Jeffamine® D-2000) | 66.1 wt % | 61.8 wt % | 58.9 wt % |
| Amine-terminated polyol (Jeffamine® T-5000) | 5.8 wt % | 5.3 wt % | 5.3 wt % |
| Ethacure® 100 | 28.1 wt % | 22.0 wt % | 17.9 wt % |
| N,N'-di-sec-butyl-[diethyl(methyl)-1,3-benzenediamine] | 0 | 11.0 wt % | 17.9 wt % |
| Mixing temperature | 71° C. | 68° C. | 59° C. |
| Gel time (cure rate) | 1 sec. | 5 sec. | 5 sec. |
| Shore D hardness, 0 sec. | 49 | 44 | 39 |
| Shore D hardness, 10 sec. | 43 | 38 | 32 |
| Tensile strength | 1880 psi ($1.30 \times 10^7$ Pa) | 1950 psi ($1.33 \times 10^7$ Pa) | 1640 psi ($1.13 \times 10^7$ Pa) |
| Elongation | 340% | 440% | 420% |
| Modulus (100%) | 1180 psi ($8.1 \times 10^6$ Pa) | 950 psi ($6.6 \times 10^6$ Pa) | 870 psi ($6.0 \times 10^6$ Pa) |
| Modulus (300%) | 1750 psi ($1.2 \times 10^7$ Pa) | 1500 psi ($1.03 \times 10^7$ Pa) | 1330 psi ($9.2 \times 10^6$ Pa) |
| Tear strength | 400 pli | 370 pli | 340 pli |

EXAMPLE 31

Polyurea formulations containing isocyanate (Rubinate® 9480, Huntsman Chemical), Jeffamine® D-2000, Jeffamine® T-5000, and N,N'-di-sec-butyl-[diethyl(methyl)-1,3-benzenediamine] were prepared as described in Example 29. Amounts of the components in each formulation are listed in Table 6; the amount of N-sec-butyl-[diethyl(methyl)-1,3-benzenediamine] listed is the amount present in the N,N'-di-sec-butyl-[diethyl(methyl)-1,3-benzenediamine]. The formulations were subjected to testing. Properties of the formulations are summarized in Table 6.

EXAMPLE 32

Polyurea formulations containing isocyanate (Rubinate® 9480, Huntsman Chemical), Jeffamine® D-2000, Jeffamine® T-5000, Ethacure® 100, and N,N'-di-sec-butyl-4,4'-methylene-bis(2,6-diethylbenzeneamine) were prepared as described in Example 29. Amounts of the components in each formulation are listed in Table 7; the amount of N-sec-butyl-4,4'-methylenebis(2,6-diethylbenzeneamine) listed is the amount present in the N,N'-di-sec-butyl-4,4'-methylenebis(2,6-diethylbenzeneamine). The formulations were subjected to testing. Properties of the formulations are summarized in Table 7.

TABLE 6

| Component | Formulation 1 | Formulation 2 | Formulation 3 | Formulation 4 | Formulation 5 |
|---|---|---|---|---|---|
| Amine-terminated polyol (Jeffamine® D-2000) | 61.8 wt % | 61.9 wt % | 62.0 wt % | 61.4 wt % | 61.5 wt % |
| Amine-terminated polyol (Jeffamine® T-5000) | 5.3 wt % | 5.3 wt % | 5.3 wt % | 5.3 wt % | 5.3 wt % |
| Ethacure® 100 | 21.9 wt % | 21.8 wt % | 21.9 wt % | 22.5 wt % | 22.4% |
| N,N'-di-sec-butyl-[diethyl(methyl)-1,3-benzenediamine] | 11.0 wt % | 11.0 wt % | 10.9 wt % | 10.9 wt % | 10.9 wt % |
| Amount of primary amine present in the secondary diamine* | 0.5% | 2.9% | 6.0% | 13.7% | 21.2% |
| Gel time (cure rate) | 9 sec. | 8 sec. | 7 sec. | 8 sec. | 10 sec. |
| Tensile strength | 1700 psi ($1.17 \times 10^7$ Pa) | 1730 psi ($1.19 \times 10^7$ Pa) | 1470 psi ($1.01 \times 10^7$ Pa) | 1270 psi ($8.76 \times 10^6$ Pa) | 1120 psi ($7.72 \times 10^6$ Pa) |
| Elongation | 390% | 400% | 300% | 260% | 220% |
| Modulus (100%) | 940 psi ($6.5 \times 10^6$ Pa) | 950 psi ($6.6 \times 10^6$ Pa) | 980 psi ($6.8 \times 10^6$ Pa) | 960 psi ($6.6 \times 10^6$ Pa) | 930 psi ($6.4 \times 10^6$ Pa) |
| Modulus (300%) | 1450 psi ($1.0 \times 10^7$ Pa) | 1460 psi ($1.0 \times 10^7$ Pa) | 1510 psi ($1.0 \times 10^7$ Pa) | 1350 psi ($9.3 \times 10^6$ Pa) | |
| Tear strength | 370 pli | 370 pli | 350 pli | 340 pli | 330 pli |

*The primary amine is N-sec-butyl-[diethyl(methyl)-1,3-benzenediamine]; the secondary diamine is N,N'-di-sec-butyl-[diethyl(methyl)-1,3-benzenediamine].

TABLE 7

| | Formulation 1 | Formulation 2 | Formulation 3 |
|---|---|---|---|
| Component | | | |
| Amine-terminated polyol (Jeffamine ® D-2000) | 57.1 wt % | 51.6 wt % | 41.6 wt % |
| Amine-terminated polyol (Jeffamine ® T-5000) | 5.9 wt % | 5.9 wt % | 5.9 wt % |
| Ethacure ® 100 | 24.3 wt % | 21.2 wt % | 15.6 wt % |
| N,N'-di-sec-butyl-4,4'-methylenebis(2,6-diethylbenzeneamine) | 12.7 wt % | 21.3 wt % | 36.9 wt % |
| Amount of primary amine present in the secondary diamine* | 3.2% | 3.2% | 3.2% |
| Property | | | |
| Gel time (cure rate) | 7 sec. | 10 sec. | 15 sec. |
| Shore D hardness, 0 sec. | 47 | 46 | 43 |
| Shore D hardness, 10 sec. | 42 | 40 | 36 |
| Tensile strength | 2010 psi ($1.39 \times 10^7$ Pa) | 2040 psi ($1.41 \times 10^7$ Pa) | 1390 psi ($9.6 \times 10^6$ Pa) |
| Elongation | 350% | 410% | 420% |
| Modulus (100%) | 1170 psi ($8.1 \times 10^6$ Pa) | 1050 psi ($7.2 \times 10^6$ Pa) | 810 psi ($5.6 \times 10^6$ Pa) |
| Modulus (300%) | 1890 psi ($1.3 \times 10^7$ Pa) | 1680 psi ($1.2 \times 10^7$ Pa) | 1180 psi ($8.1 \times 10^6$ Pa) |
| Tear strength | 425 pli | 400 pli | 310 pli |

*The primary amine is N-sec-butyl-4,4'-methylenebis(2,6-diethylbenzeneamine), a monosubstituted product; the secondary diamine is N,N'-di-sec-butyl-4,4'-methylenebis(2,6-diethylbenzeneamine).

Formulations similar to the those in Examples 29-32 were made with N,N'-diisopropyl-4,4'-methylenebis(benzeneamine) and N,N'-di-5-nonyl-isophoronediamine. The gel time (cure rate) for the N,N'-diisopropyl-4,4'-methylenebis(benzeneamine) formulation was 300 seconds, and the gel time for the N,N'-di-5-nonyl-isophoronediamine formulation was 59 seconds. Another formulation similar to those in Examples 29-32 was made with N,N'-di-2-(4-methylpentyl)-isophoronediamine; the gel time for this formulation was 22 seconds. Still another formulation similar to those in Examples 29-32 was made with N,N'-di-(3,3-dimethyl-2-butyl)-TCD diamine; the gel time for this formulation was 25 seconds. Yet another formulation similar to those in Examples 29-32 was made with N,N'-di-(3,3-dimethyl-2-butyl)-1,6-diaminohexane; the gel time for this formulation was 25 seconds at room temperature. In addition, curing agents having up to about 10% (or even 15%) of the corresponding mono-secondary-diamine (in which one of the amino groups is secondary and the other amino group is primary) have been found to be effective in formulations similar to those in Examples 29-32.

EXAMPLE 33

Polyurea formulations containing isocyanate (Rubinate® 9480, Huntsman Chemical), Jeffamine® D-2000, Jeffamine® T-5000, Ethacure® 100, N,N'-diethyl-4,4'-methylenebis-(benzeneamine), N,N'-diethyl-4,4'-methylenebis (benzeneamine) containing 29% of atriamine (N,N',N"-triethyl-4-(methyl-4'-benzeneamine)-2-(methyl-4"-benzeneamine)-1-aminobenzene), or N,N'-di-[2-(4-methylpentyl)]isophorone diamine were prepared as described in Example 29. One formulation was prepared using only Ethacure® 100, for comparative purposes. Amounts of the components in each formulation are listed in Table 8. The formulations were subjected to testing. Properties of the formulations are summarized in Table 8.

TABLE 8

| Component | Formulation 1 | Formulation 2 | Formulation 3 | Formulation 4 |
|---|---|---|---|---|
| Amine-terminated polyol (Jeffamine ® D-2000) | 66.1 wt % | 51.5 wt % | 51.5 wt % | 37.7 wt % |
| Amine-terminated polyol (Jeffamine ® T-5000) | 5.8 wt % | 5.3 wt % | 5.3 wt % | 5.2 wt % |
| Ethacure ® 100 | 28.1 wt % | 0 | 0 | 0 |
| Amount of aromatic secondary diamine | 0 | 43.2 wt % | 43.2 wt % | 57.1 wt % |
| Aromatic secondary diamine | | N,N'-diethyl-4,4'-methylenebis(benzene amine) | N,N'-diethyl-4,4'-methylenebis(benzene amine) + triamine | N,N'-di-[2-(4-methylpentyl)]isophorone diamine |
| Triamine | 0 | 0 | (29%) | 0 |
| Gel time (cure rate) | <2 sec. | 61 sec. | 61 sec. | 97 sec. |
| Shore D hardness, 0 sec | 45 | 28 | 38 | 44 |
| Shore D hardness, 10 sec | 40 | 23 | 34 | 38 |
| Tensile strength | 2310 psi | 1060 psi | 1960 psi | 2030 psi |
| Elongation | 370% | 470% | 280% | 370% |
| Modulus (100%) | 1300 psi | 520 psi | 1045 psi | 990 psi |
| Modulus (300%) | 2030 psi | 800 psi | 2070 psi | 1720 psi |
| Tear strength | 460 pli | 240 pli | 300 pli | 470 pli |

EXAMPLE 34

Polyurea formulations containing isocyanate (Rubinate® 9480, Huntsman Chemical), Jeffamine® D-2000, Jeffamine® T-5000, Ethacure® 100, N,N'-diethyl-4,4'-methylenebis-(benxeneamine), N,N'-diethyl-4,4'-methylenebis(benzeneamine) containing 29% of a triamine (N,N',N''-triethyl-4-(methyl-4'-benzeneamine)-2-(methyl-4''-benzeneamine)-1-aminobenzene), or N,N'-di-[2-(4-methylpentyl)]isophorone diamine were prepared as described in Example 29; one formulation was prepared without a secondary diamine of this invention, for comparative purposes. Amounts of the components in each formulation are listed in Table 9. The formulations were subjected to testing. Properties of the formulations are summarized in Table 9.

TABLE 9

| Component | Formulation 1 | Formulation 2 | Formulation 3 |
| --- | --- | --- | --- |
| Amine-terminated polyol (Jeffamine ® D-2000) | 60.0 wt % | 60.0 wt % | 57.2 wt % |
| Amine-terminated polyol (Jeffamine ® T-5000) | 5.4 wt % | 5.4 wt % | 5.2 wt % |
| Ethacure ® 100 | 17.3 wt % | 17.3 wt % | 18.8 wt % |
| Amount of aromatic secondary diamine | 17.3 wt % | 17.3 wt % | 18.8 wt % |
| Aromatic secondary diamine | N,N'-diethyl-4,4'-methylenebis(benzene amine) | N,N'-diethyl-4,4'-methylenebis(benzeneamine) + triamine | N,N'-di-[2-(4-methylpentyl)]isophorone diamine |
| Gel time (cure rate) | 11 sec. | 10 sec. | 14 sec. |
| Shore D hardness, 0 sec | 36 | 36 | 45 |
| Shore D hardness, 10 sec | 33 | 34 | 41 |
| Tensile strength | 1740 psi | 2530 psi | 2670 psi |
| Elongation | 330% | 340% | 390% |
| Modulus (100%) | 1080 psi | 1310 psi | 1360 psi |
| Modulus (300%) | 1650 psi | 2280 psi | 2350 psi |
| Tear strength | 370 pli | 390 pli | 520 pli |

EXAMPLE 35

Polyurea formulations containing isocyanate (Rubinate® 9480 or Rubinate® 9009, Huntsman Chemical), Jeffamine® D-2000, Jeffamine® T-5000, and N,N'-diethyl-4,4'-methylenebis(benzeneamine) were prepared as described in Example 28. Amounts of the components in each formulation are listed in Table 10. The formulations were subjected to testing. Properties of the formulations are summarized in Table 10.

TABLE 10

| Component | Formulation 1 | Formulation 2 |
| --- | --- | --- |
| Isocyanate | Rubinate ® 9480 | Rubinate ® 9009 |
| Amine-terminated polyol (Jeffamine ® D-2000) | 51.5 wt % | 50.4 wt % |
| Amine-terminated polyol (Jeffamine ® T-5000) | 5.3 wt % | 5.4 wt % |
| Amount of N,N'-diethyl-4,4'-methylenebis(benzeneamine) | 43.2 wt % | 44.3 wt % |
| Gel time (cure rate) | 53 sec. | 17 sec. |
| Shore D hardness, 0 sec | 29 | 50 |
| Shore D hardness, 10 sec | 20 | 44 |
| Tensile strength | 920 psi | 2280 psi |
| Elongation | 420% | 130% |
| Modulus (100%) | 518 psi | 2080 psi |
| Modulus (300%) | 770 psi | |
| Tear strength | 250 pli | 440 pli |

EXAMPLE 36

Polyurea formulations containing isocyanate (Rubinate® 9480, Huntsman Chemical), Jeffamine® D-2000, Jeffamine® T-5000, Ethacure® 100, and/or N,N'-di-(3,3-dimethyl-2-butyl)-TCD diamine were prepared as described in Example 29. One formulation was prepared using only Ethacure® 100, for comparative purposes. Amounts of the components in each formulation are listed in Table 11. The formulation having N,N'-di-(3,3-dimethyl-2-butyl)-TCD diamine without Ethacure® 100 was observed to be brittle. The formulations were subjected to testing. Properties of the formulations are summarized in Table 11.

TABLE 11

| Component | Formulation 1 | Formulation 2 | Formulation 3 |
| --- | --- | --- | --- |
| Amine-terminated polyol (Jeffamine ® D-2000) | 66.1 wt % | 49.5 wt % | 31.3 wt % |
| Amine-terminated polyol (Jeffamine ® T-5000) | 5.8 wt % | 5.8 wt % | 5.7 wt % |
| Ethacure ® 100 | 28.1 wt % | 14.7 wt % | 0 |
| Amount of diamine | 0 | 30.0 wt % | 63.0 wt % |
| Gel time (cure rate) | <2 sec. | 11 sec. | 50 sec. |
| Shore D hardness, 0 sec | 45 | 47 | 57 |
| Shore D hardness, 10 sec | 40 | 43 | 55 |
| Tensile strength | 2310 psi | 2500 psi | 2410 psi |
| Elongation | 370% | 360% | 280% |
| Modulus (100%) | 1300 psi | 1340 psi | 1570 psi |
| Modulus (300%) | 2030 psi | 2250 psi | 1790 psi |
| Tear strength | 460 pli | 500 pli | 630 pli |

It is to be understood that the reactants and components referred to by chemical name or formula anywhere in this document, whether referred to in the singular or plural, are identified as they exist prior to coming into contact with another substance referred to by chemical name or chemical type (e.g., another reactant, a solvent, or etc.). It matters not what preliminary chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. Thus the reactants and components are identified as ingredients to be brought together in connection with performing a desired chemical operation or reaction or in forming a mixture to be used in conducting a desired operation or reaction. Also, even though an embodiment may refer to substances, components and/or ingredients in the present tense ("is comprised of", "comprises", "is", etc.), the reference is to the substance, component or ingredient as it existed at the time just before it was first contacted, blended or mixed with one or more other substances, components and/or ingredients in accordance with the present disclosure.

Also, even though the may refer to substances in the present tense (e.g., "comprises", "is", etc.), the reference is to the substance as it exists at the time just before it is first contacted, blended or mixed with one or more other substances in accordance with the present disclosure.

Except as may be expressly otherwise indicated, the article "a" or "an" if and as used herein is not intended to limit, and should not be construed as limiting, the description or a to a single element to which the article refers. Rather, the article "a" or "an" if and as used herein is intended to cover one or more such elements, unless the text expressly indicates otherwise.

Each and every patent or other publication or published document referred to in any portion of this specification is incorporated in toto into this disclosure by reference, as if fully set forth herein.

This invention is susceptible to considerable variation in its practice.

The invention claimed is:

1. An aliphatic secondary diamine which is N,N'-di-(3,3-dimethyl-2-butyl)-1,6-diaminohexane.

* * * * *